(12) United States Patent
Miesel et al.

(10) Patent No.: US 8,447,401 B2
(45) Date of Patent: *May 21, 2013

(54) COLLECTING POSTURE INFORMATION TO EVALUATE THERAPY

(75) Inventors: Keith A. Miesel, St. Paul, MN (US); Kenneth T. Heruth, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 218 days.

This patent is subject to a terminal disclaimer.

(21) Appl. No.: 12/856,255

(22) Filed: Aug. 13, 2010

(65) Prior Publication Data

US 2010/0305665 A1 Dec. 2, 2010

Related U.S. Application Data

(63) Continuation of application No. 11/691,391, filed on Mar. 26, 2007, now Pat. No. 7,792,583, which is a continuation-in-part of application No. 11/081,872, filed on Mar. 16, 2005, now Pat. No. 7,447,545, which is a continuation-in-part of application No. 10/826,926, filed on Apr. 15, 2004, now Pat. No. 7,330,760.

(60) Provisional application No. 60/553,784, filed on Mar. 16, 2004, provisional application No. 60/785,820, filed on Mar. 24, 2006.

(51) Int. Cl.
*A61N 1/36* (2006.01)

(52) U.S. Cl.
USPC ............................................................ 607/19

(58) Field of Classification Search
USPC .......................................... 607/17–19, 45, 49
See application file for complete search history.

(56) References Cited

U.S. PATENT DOCUMENTS

| 4,297,685 A | 10/1981 | Brainard, II |
| 4,550,736 A | 11/1985 | Broughton et al. |

(Continued)

FOREIGN PATENT DOCUMENTS

| DE | 198 31 109 | 1/2000 |
| DE | 100 24 103 | 11/2001 |

(Continued)

OTHER PUBLICATIONS

Amzica, "Physiology of Sleep and Wakefulness as it Relates to the Physiology of Epilepsy," Journal of Clinical Neurophysiology, American Clinical Neurophysiology Society, 19(6), pp. 488-503, (2002).

(Continued)

*Primary Examiner* — Rex R Holmes
(74) *Attorney, Agent, or Firm* — Shumaker & Sieffert, P.A.

(57) ABSTRACT

A medical device delivers a therapy to a patient. Posture events are identified, e.g., a posture of the patient is periodically determined and/or posture transitions by the patient are identified, and each determined posture event is associated with a current therapy parameter set. A value of at least one posture metric is determined for each of a plurality of therapy parameter sets based on the posture events associated with that therapy parameter set. A list of the therapy parameter sets is presented to a user, such as a clinician, for evaluation of the relative efficacy of the therapy parameter sets. The list may be ordered according to the one or more posture metric values to aid in evaluation of the therapy parameter sets. Where values are determined for a plurality of posture metrics, the list may be ordered according to the one of the posture metrics selected by the user.

20 Claims, 11 Drawing Sheets

U.S. PATENT DOCUMENTS

| | | |
|---|---|---|
| 4,771,780 A | 9/1988 | Sholder |
| 4,776,345 A | 10/1988 | Cohen et al. |
| 4,846,195 A | 7/1989 | Alt |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,233,984 A | 8/1993 | Thompson |
| 5,275,159 A | 1/1994 | Griebel |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,514,162 A | 5/1996 | Bornzin et al. |
| 5,593,431 A | 1/1997 | Sheldon |
| 5,622,428 A | 4/1997 | Bonnet |
| 5,645,053 A | 7/1997 | Remmers et al. |
| 5,732,696 A | 3/1998 | Rapoport et al. |
| 5,782,884 A | 7/1998 | Stotts et al. |
| 5,895,371 A | 4/1999 | Levitas et al. |
| 5,904,708 A | 5/1999 | Goedeke |
| 5,919,149 A | 7/1999 | Allum |
| 5,941,906 A | 8/1999 | Barreras, Sr. et al. |
| 5,944,680 A | 8/1999 | Christopherson et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,165,143 A | 12/2000 | van Lummel |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,315,740 B1 | 11/2001 | Singh |
| 6,351,672 B1 | 2/2002 | Park et al. |
| 6,366,813 B1 | 4/2002 | DiLorenzo |
| 6,416,471 B1 | 7/2002 | Kumar et al. |
| 6,433,690 B2 | 8/2002 | Petelenz et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,514,218 B2 | 2/2003 | Yamamoto |
| 6,539,249 B1 | 3/2003 | Kadhiresan et al. |
| 6,574,507 B1 | 6/2003 | Bonnet |
| 6,605,038 B1 | 8/2003 | Teller et al. |
| 6,611,783 B2 | 8/2003 | Kelly, Jr. et al. |
| 6,659,968 B1 | 12/2003 | McClure |
| 6,687,538 B1 | 2/2004 | Hrdlicka et al. |
| 6,731,984 B2 | 5/2004 | Cho et al. |
| 6,735,474 B1 | 5/2004 | Loeb et al. |
| 6,752,766 B2 | 6/2004 | Kowallik et al. |
| 6,773,404 B2 | 8/2004 | Poezevera et al. |
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,964,641 B2 | 11/2005 | Cho et al. |
| 6,997,882 B1 | 2/2006 | Parker et al. |
| 7,162,304 B1 | 1/2007 | Bradley |
| 7,209,787 B2 | 4/2007 | DiLorenzo |
| 7,313,440 B2* | 12/2007 | Miesel .............. 607/19 |
| 7,330,760 B2* | 2/2008 | Heruth et al. .................. 607/17 |
| 7,369,896 B2* | 5/2008 | Gesotti .......................... 607/49 |
| 7,447,575 B2* | 11/2008 | Goldbeck et al. ............ 701/36 |
| 7,792,583 B2* | 9/2010 | Miesel et al. .............. 607/19 |
| 2001/0037067 A1 | 11/2001 | Tchou et al. |
| 2001/0049471 A1 | 12/2001 | Suzuki et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0177882 A1 | 11/2002 | DiLorenzo |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0102814 A1 | 5/2004 | Sorensen et al. |
| 2004/0111040 A1 | 6/2004 | Ni et al. |
| 2004/0111041 A1 | 6/2004 | Ni et al. |
| 2004/0199217 A1 | 10/2004 | Lee et al. |
| 2005/0021103 A1 | 1/2005 | DiLorenzo |
| 2005/0021104 A1 | 1/2005 | DiLorenzo |
| 2005/0042589 A1 | 2/2005 | Hatlestad et al. |
| 2005/0060001 A1* | 3/2005 | Singhal et al. .................. 607/19 |
| 2005/0113710 A1 | 5/2005 | Stahmann et al. |
| 2005/0119703 A1 | 6/2005 | DiLorenzo |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222626 A1 | 10/2005 | DiLorenzo |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2005/0245988 A1 | 11/2005 | Miesel |
| 2006/0224191 A1 | 10/2006 | DiLorenzo |
| 2006/0293720 A1 | 12/2006 | DiLorenzo |
| 2007/0046408 A1 | 3/2007 | Shim |
| 2007/0073355 A1 | 3/2007 | DiLorenzo |
| 2007/0142862 A1 | 6/2007 | DiLorenzo |

FOREIGN PATENT DOCUMENTS

| | | |
|---|---|---|
| EP | 0 564 803 A1 | 10/1993 |
| EP | 0 849 715 B1 | 6/1998 |
| EP | 1 195 139 A1 | 4/2002 |
| EP | 1 291 036 A2 | 3/2003 |
| EP | 1 308 182 A2 | 5/2003 |
| EP | 1 437 159 A1 | 7/2004 |
| EP | 1 322 227 B1 | 12/2005 |
| GB | 2 330 912 A | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/041771 | 5/2002 |
| WO | WO 02/087433 | 11/2002 |
| WO | WO 02/096512 | 12/2002 |
| WO | WO 02/100267 | 12/2002 |
| WO | WO 03/024325 | 3/2003 |
| WO | WO 03/051356 | 6/2003 |
| WO | WO 03/065891 | 8/2003 |
| WO | WO 2005/028029 | 3/2005 |
| WO | WO 2005/035050 | 4/2005 |

OTHER PUBLICATIONS

Dinner, "Effect of Sleep on Epilepsy," Journal of Clinical Neurophysiology, American Clinical Neurophysiology Society, 19(6), pp. 504-513, (2002).

Mendez et al. "Interactions Between Sleep and Epilepsy," Journal of Clinical Neurophysiology, American Clinical Neurophysiology Society, 18(2), pp. 106-127, (2001).

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).

"MiniMitter® Physiological and Behavioral Monitoring for Humans and Animals," http://www.minimitter.com/Products/Actiwatch, 3 pgs. Feb. 20, 2006.

"IBM & Citzen Watch develop Linux-based 'WatchPad'," 5 pgs., http://www.linuxdevices.com/news/NS6580187845.html, Feb. 20, 2006.

"Design Competition: Runners-Up for the Best Three Designs," EPN, vol. 26, No. 1, 1 pg., (2002).

"Watch," Wikipedia, the free encyclopedia, 6 pgs., http://en.wikipedia.org/wiki/Watch, Feb. 20, 2006.

Kassam, "2005 EDP Topic 'MK4': Tremor Data-Logger for Parkinson's Disease Patients," http://www.ee.ryerson.ca/~courses/edp2005/MK4.html, 3 pgs., Feb. 20, 2006.

Tuisku, "Motor Activity Measured by Actometry in Neuropsychiatric Disorders," Department of Psychiatry, University of Helsinski, Helsinki, Finland, 115 pgs. (2002).

Smith et al., "Presleep Cognitions in Patients with Insomnia Secondary to Chronic Pain," Journal of Behavioral Medicine, vol. 24, No. 1, pp. 93-114, (2001).

Smith et al. "How do sleep disturbance and chronic pain inter-relate? Insights from the longitudinal and cognitive-behavioral clinical trials literature," Sleep Medicine Reviews, YSMRV 286, pp. 1-14, (2003).

Goodrich et al., "The Prediction of Pain Using Measures of Sleep Quality," Pain Digest, 8:23-25, (1998).

"Analysis of heart rate dynamics by methods derived from nonlinear mathematics: Clinical applicability and prognostic significance" http:/herkules.oulu.fi.isbn9514250133/html, 4 pgs., (2004).

Kerr et al., "Analysis of the sit-stand-sit movement cycle in normal subjects," Clinical Biomechanics, vol. 12, No. 4, pp. 236-245, (1997).

Aminian et al. "Physical Activity Monitoring Based on Accelerometry: Validation and Comparison with Video Observation," Medical & Biological Engineering & Computing, vol. 37, No. 2, pp. 304-308 (1999).

Medcare—A Global Leader in Sleep Diagnostics, Embletta Recording System, http://www.medcare.com/products/diagnostic/embletta/, 2 pgs. Jan. 31, 2005.

Medcare—A Global Leader in Sleep Diagnostics, Somnologica for Embletta, http://www.medcare.com/products/diagnostic/embletta/SomnoEmbletta/index.asp, 1 pg. Jan. 31, 2005.

MAP Medizin-Technologie GmbH, Poly-MESAM®, http://195.244.124.130/map/de/eng/map_med.nsf/smsall/70564A3FCBE4188AC1256EF4.., 4 pgs. Jan. 31, 2005.

Merlin, http://www.aha.ru/~pir/english/merlin/, 4 pgs. Jan. 31, 2005.

Sleep Solutions—PR Newswire: Sleep Solutions Introduces NovaSom™ QSG™ for PSG . . , http://www.sleep-solutions.com/press_room/novasom.htm, 2 pgs. Jan. 31, 2005.

Itamar Medical Information, http://itamar-medical.com/content.asp?id-id=31, 2 pgs. Jan. 31, 2005.

Criticare System Inc.,-504DX Portable Pulse Oximeter, http://www.csiusa.com/504dx.html, 4 pgs. Jan. 31, 2005.

Snap® Laboratories, Product Fact Sheet, http://www.snaplab.com/mp_fact.htm, 2 pgs. Jan. 31, 2005.

Sleep Strip & Bite Strip, http://ww.quietsleep.com/snoringapnea/sleepstrip.htm, 8 pgs. Jan. 31, 2005.

"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.

"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.

"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.

Office Action dated Aug. 4, 2009 for U.S. Appl. No. 11/413,619 (9 pgs.).

Response dated Nov. 4, 2009 for U.S. Appl. No. 11/413,619 (7 pgs.).

Office Action dated Feb. 25, 2008 for U.S. Appl. No. 11/081,872 (5 pgs.).

Response to Office Action dated May 27, 2008 for U.S. Appl. No. 11/081,872 (2 pgs.).

Office Action dated Mar. 11, 2009 for U.S. Appl. No. 10/826,926 (25 pgs.).

Responsive Amendment dated Aug. 11, 2009 for U.S. Appl. No. 10/826,925 (12 pgs.).

Office Action dated May 8, 2009 for U.S. Appl. No. 11/691,391 (8 pgs.).

Responsive Amendment dated Aug. 5, 2009 for U.S. Appl. No. 11/691,391 (10 pgs.).

Office Action dated May 29, 2009 for U.S. Appl. No. 11/081,811 (13 pgs.).

Responsive Amendment dated Aug. 31, 2009 for U.S. Appl. No. 11/081,811 (17 pgs.).

Office Action dated Dec. 31, 2009 for U.S. Appl. No. 11/691,391 (6 pgs.).

Response dated Mar. 31, 2010 for U.S. Appl. No. 11/691,391 (5 pgs.).

Office Action dated Aug. 5, 2010 for U.S. Appl. No. 12/248,609 (8 pgs.).

Response dated Nov. 4, 2010 for U.S. Appl. No. 12/248,609 (10 pgs.).

Office Action dated Sep. 29, 2010 for U.S. Appl. No. 12/248,622, (7 pgs.).

Response dated Nov. 18, 2010 for U.S. Appl. No. 12/248,622, (10 pgs.).

Office Action dated Dec. 22, 2010 for U.S. Appl. No. 12/248,609, (7 pgs.).

Advisory Action dated Feb. 28, 2011 for U.S. Appl. No. 12/248,609, (3 pgs.).

Notice of Appeal and Pre-Appeal Brief Request for Review dated Mar. 22, 2011 for U.S. Appl. No. 12/248,609, (6 pgs.).

Office Action dated May 10, 2011 for U.S. Appl. No. 12/248,622, (6 pgs.).

Responsive Amendment dated Aug. 10, 2011 for U.S. Appl. No. 12/248,622, (10 pgs.).

Office Action dated May 10, 2011 for U.S. Appl. No. 12/248,609, (7 pgs.).

Responsive Amendment dated Aug. 10, 2011 for U.S. Appl. No. 12/248,609, (11 pgs.).

Response to Office Action dated Jul. 26, 2012, from U.S. Appl. No. 13/362,785, filed Oct. 23, 2012, 6 pp.

Final Office Action dated Oct. 20, 2011 for U.S. Appl. No. 12/248,622, (8 pgs.).

Response dated Dec. 20, 2011 for U.S. Appl. No. 12/248,622, (5 pgs.).

Final Office Action dated Oct. 20, 2011 for U.S. Appl. No. 12/248,609, (8 pgs.).

Response dated Dec. 20, 2011 for U.S. Appl. No. 12/248,609, (7 pgs.).

\* cited by examiner

| PARAMETER SET | PARAMETERS | % UPRIGHT | TRANSITIONS/HOUR |
|---|---|---|---|
| 1 | PA = 5.5V<br>PW = 210ms<br>PR = 90Hz | 75% | 15 |
| 2 | PA = 5V<br>PW = 190ms<br>PR = 95Hz | 60% | 9 |
| ••• | | | |
| N | PA = 4.6V<br>PW = 215ms<br>PR = 80Hz | 55% | 8 |

FIG. 7

COLLECTING POSTURE INFORMATION TO EVALUATE THERAPY

This application is a continuation of U.S. application Ser. No. 11/691,391, filed Mar. 26, 2007, issued as U.S. Pat. No. 7,792,583, which is a continuation-in-part of U.S. application Ser. No. 11/081,872, filed Mar. 16, 2005, issued as U.S. Pat. No. 7,447,545, which was a continuation-in-part of U.S. application Ser. No. 10/826,926, filed Apr. 15, 2004, issued as U.S. Pat. No. 7,330,760, which claimed the benefit of U.S. provisional application No. 60/553,784, filed Mar. 16, 2004. U.S. application Ser. No. 11/691,391 also claimed the benefit of U.S. Provisional Application No. 60/785,820, filed Mar. 24, 2006. The entire content of each of these applications is incorporated herein by reference.

TECHNICAL FIELD

The invention relates to medical devices and, more particularly, to medical devices that deliver therapy.

BACKGROUND

In some cases, an ailment may affect a patient's activity level or range of activities by preventing the patient from being active. For example, chronic pain may cause a patient to avoid particular physical activities, or physical activity in general, where such activities increase the pain experienced by the patient. Other ailments that may affect patient activity include movement disorders such as tremor, Parkinson's disease, multiple sclerosis, epilepsy, or spasticity, which may result in irregular movement or activity, other neurological disorders, or a generally decreased level of activity. The difficulty walking or otherwise moving experienced by patients with movement disorders may cause such patients to avoid movement to the extent possible. Further, depression or other psychological disorders such as depression, mania, bipolar disorder, or obsessive-compulsive disorder, congestive heart failure, cardiac arrhythmia, gastrointestinal disorders, and incontinence are other examples of disorders that may generally cause a patient to be less active. When a patient is inactive, he may be more likely to be recumbent, i.e., lying down, or sitting, and may change postures less frequently.

In some cases, these ailments are treated via a medical device, such as an implantable medical device (IMD). For example, patients may receive an implantable neurostimulator or drug delivery device to treat chronic pain, a movement disorder, or a psychological disorder. Congestive heart failure and arrhythmia may be treated by, for example, a cardiac pacemaker or drug delivery device.

SUMMARY

In general, the invention is directed to techniques for evaluating a therapy delivered to a patient by a medical device based on posture information. At any given time, the medical device delivers the therapy according to a current set of therapy parameters. The therapy parameters may change over time such that the therapy is delivered according to a plurality of different therapy parameter sets. The medical device, or another device, may identify posture events based on the posture of the patient, e.g., periodically identify the patient's posture and/or posture transitions. The posture events may be associated with the current therapy parameter set when the event is identified. A value of at least one posture metric is determined for each of the therapy parameter sets based on the posture events associated with that parameter set. A list of the therapy parameter sets and associated posture metrics is presented to a user, such as clinician, for evaluation of the relative efficacy of the therapy parameter sets. The list may be ordered according to the posture metric values to aid in evaluation of the therapy parameter sets. In this manner, the user may readily identify the therapy parameter sets that support the highest activity levels for the patient, and evaluate the relative efficacy of the parameter sets.

The therapy delivering medical device or another device may monitor one or more signals that are generated by respective sensors and vary as a function of patient posture. For example, the medical device or other device may monitor signals generated by a plurality of accelerometers, gyros, or magnetometers. The sensors may be oriented substantially orthogonally with each other, and each sensor may be substantially aligned with a body axis of the patient. The therapy may be designed to treat a neurological disorder of the patient. Example therapies may include a movement disorder therapy, a psychological disorder therapy, or deep brain stimulation therapy. Specific neurological disorders may include Parkinson's disease or epilepsy.

The medical device or other device may identify a plurality of posture events based on the one or more signals. In some embodiments, the device periodically identifies the posture of the patient based on the one or more signals, and the identified posture is stored as a posture event. The device may identify whether the patient is upright or recumbent, e.g., lying down. In some embodiments in which sensors are located at a plurality of positions on or within the body of the patient, the device may be able to identify additional postures, such as standing, sitting and recumbent. Example locations for the sensors include on or with the trunk of the patient, e.g., within an implantable medical device in the abdomen of the patient, and additionally, in some embodiments, on or within an upper leg of the patient. In some embodiments, the device identifies transitions between postures, and stores indications of posture transitions as posture events.

As mentioned above, each posture event may be associated with a current set of therapy parameters and, for each of a plurality of therapy parameter sets used by the medical device over time, a value of one or more posture metrics may be determined. A posture metric value may be, for example, an amount or percentage of time spent in a posture while a therapy parameter set is active, e.g., average amount of time over a period of time, such as an hour, that a patient was within a particular posture. In some embodiments, a posture metric value may be an average number of posture transitions over a period of time, e.g., an hour, that a particular therapy parameter sets was active.

In embodiments in which a plurality of posture metrics are determined for each therapy parameter set, an overall posture metric may be determined based on the plurality of posture metrics. The plurality of posture metrics may be used as indices to select an overall posture metric from a look-up table comprising a scale of potential overall posture metrics. The scale may be numeric, such as overall posture metric values from 1-10.

A computing device, such as a programming device, or, in some external medical device embodiments, the medical device itself, presents a list of the plurality of parameter sets and associated posture metric values via a display. The computing device may order the list according to the posture metric values. Where values are determined for a plurality of posture metrics for each of the therapy parameter sets, the programming device may order the list according to the values of a user selected one of the posture metrics. The computing device may also present other posture information to a user, such as a trend diagram of identified postures over time, or a histogram or pie chart illustrating percentages of time that the patient assumed certain postures. The computing device may generate such charts or diagrams using posture events associated with a particular one of the therapy parameter sets, or all of the posture events identified by the medical device.

In one embodiment, the invention is directed to a method for evaluating therapy which includes monitoring a signal generated by a sensor as a function of posture of a patient and identifying a plurality of posture events based on the signal. The method also includes associating each of the posture events with a therapy parameter set currently used by a medical device to deliver a therapy to the patient when the posture event is identified, wherein the therapy comprises at least one of a movement disorder therapy, psychological disorder therapy, or deep brain stimulation and determining a value of a posture metric for each of a plurality of therapy parameter sets based posture events associated with the therapy parameter sets.

In another embodiment, the invention is directed to a medical system that includes a medical device that delivers at least one of a movement disorder therapy, psychological disorder therapy, or deep brain stimulation to a patient and a sensor that generates a signal as a function of posture of the patient. The medical system also includes a processor that monitors the signal generated by the sensor, identifies a plurality of posture events based on the signal, associates each of the posture events with a therapy parameter set currently used by the medical device to deliver the at least one of the movement disorder therapy, psychological disorder therapy, or deep brain stimulation to the patient when the posture event is identified, and determines a value of a posture metric for each of a plurality of therapy parameter sets based posture events associated with the therapy parameter sets.

In an additional embodiment, the invention is directed to a medical system that includes means for delivering at least one of a movement disorder therapy, psychological disorder therapy, or deep brain stimulation to a patient and means for monitoring a signal generated by a sensor as a function of posture of a patient. The medical system also includes means for identifying a plurality of posture events based on the signal, means for associating each of the posture events with a therapy parameter set currently used by the means for delivering to deliver the at least one of the movement disorder therapy, psychological disorder therapy, or deep brain stimulation to a patient when the activity level is determined, and means for determining a value of a posture metric for each of a plurality of therapy parameter sets based posture events associated with the therapy parameter sets.

The invention is capable of providing one or more advantages. For example, a medical system according to the invention may provide a clinician with an objective indication of the efficacy of different sets of therapy parameters. Further, by displaying therapy parameter sets and associated posture metric values in an ordered and, in some cases, sortable list, the medical system may allow the clinician to more easily compare the relative efficacies of a plurality of therapy parameter sets. The medical system may be particularly useful in the context of trial neurostimulation for treatment of, for example, chronic pain or neurological disorders, where the patient is encouraged to try a plurality of therapy parameter sets to allow the patient and clinician to identify efficacious therapy parameter sets.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 7 illustrates an example list of therapy parameter sets and associated activity metric values that may be presented by a clinician programmer.

DETAILED DESCRIPTION

Figure 1A:
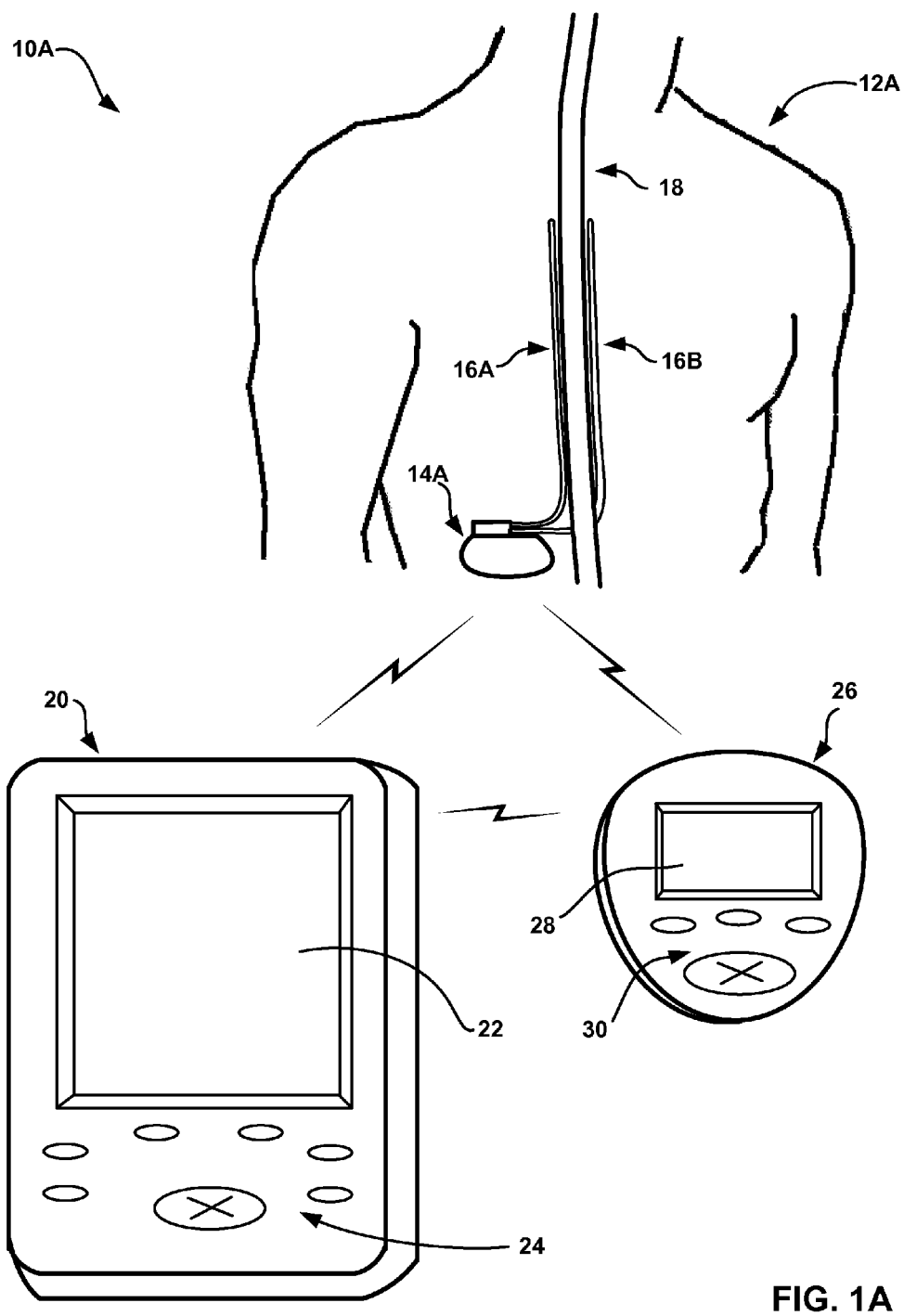
FIGS. 1A and 1B are conceptual diagrams illustrating example systems that include an implantable medical device that collects activity information according to the invention.
Figure 1B:
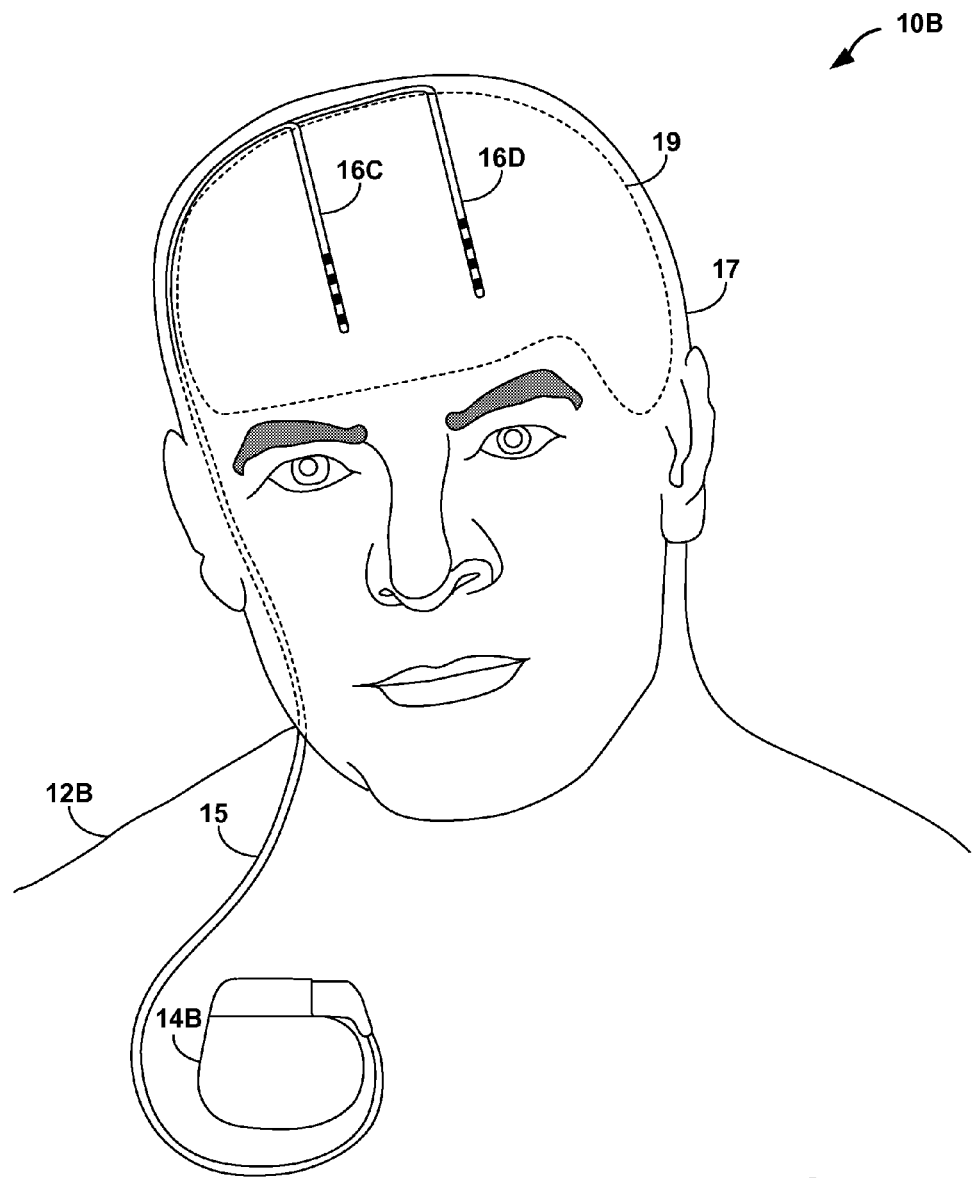

FIGS. 1A and 1B are conceptual diagrams illustrating example systems 10A and 10B (collectively "systems 10") that respectively include an implantable medical device (IMD) 14A or 14B (collectively "IMDs 14") that collect information relating to the posture of a respective one of patients 12A and 12B (collectively "patients 12"). In the illustrated example systems 10A and 10B, IMDs 14 takes the form of an implantable neurostimulator that delivers neurostimulation therapy in the form of electrical pulses or signals to a patient 12. However, the invention is not limited to implementation via an implantable neurostimulator. For example, in some embodiments of the invention, IMDs 14 may take the form of an implantable pump or implantable cardiac rhythm management device, such as a pacemaker, that collects posture information. Further, the invention is not limited to implementation via an IMD. In other words, any implantable or external medical device may collect activity information according to the invention.

In the illustrated example, IMDs 14A and 14B delivers neurostimulation therapy to patients 12A and 12B via leads 16A and 16B, and leads 16B and 16D (collectively "leads 16"), respectively. Leads 16A and 16B may, as shown in FIG. 1A, be implanted proximate to the spinal cord 18 of patient 12A, and IMD 14A may deliver spinal cord stimulation (SCS) therapy to patient 12A in order to, for example, reduce pain experienced by patient 12A. However, the invention is not limited to the configuration of leads 16A and 16B shown in FIG. 1A or the delivery of SCS or other pain therapies.

For example, in another embodiment, illustrated in FIG. 1B, leads 16C and 16D may extend to brain 19 of patient 12B, e.g., through cranium 17 of patient. IMD 14B may deliver deep brain stimulation (DBS) or cortical stimulation therapy to patient 12 to treat any of a variety of non-respiratory neurological disorders, such as movement disorders or psychological disorders. Non-respiratory neurological disorders exclude respiratory disorders, such as sleep apnea. Example therapies may treat tremor, Parkinson's disease, spasticity, epilepsy, depression or obsessive-compulsive disorder. As illustrated in FIG. 1B, leads 16C and 16D may be coupled to IMD 14B via one or more lead extensions 15.

As further examples, one or more leads 16 may be implanted proximate to the pelvic nerves (not shown) or stomach (not shown), and an IMD 14 may deliver neurostimulation therapy to treat incontinence or gastroparesis. Additionally, leads 16 may be implanted on or within the heart to treat any of a variety of cardiac disorders, such as congestive heart failure or arrhythmia, or may be implanted proximate to any peripheral nerves to treat any of a variety of disorders, such as peripheral neuropathy or other types of chronic pain.

The illustrated numbers and locations of leads 16 are merely examples. Embodiments of the invention may include any number of lead implanted at any of a variety of locations within a patient. Furthermore, the illustrated number and location of IMDs 14 are merely examples. IMDs 14 may be located anywhere within patient according to various embodiments of the invention. For example, in some embodiments, an IMD 14 may be implanted on or within cranium 17 for delivery of therapy to brain 19, or other structure of the head of the patient 12.

IMDs 14 delivers therapy according to a set of therapy parameters, i.e., a set of values for a number of parameters that define the therapy delivered according to that therapy parameter set. In embodiments where an IMD 14 delivers neurostimulation therapy in the form of electrical pulses, the parameters of each parameter set may include voltage or current pulse amplitudes, pulse widths, pulse rates, duration, duty cycle, and the like. Further, each of leads 16 includes electrodes (not shown in FIG. 1), and a therapy parameter set may include information identifying which electrodes have been selected for delivery of pulses, and the polarities of the selected electrodes. In embodiments in which IMDs 14 deliver other types of therapies, therapy parameter sets may include other therapy parameters such as drug concentration and drug flow rate in the case of drug delivery therapy. Therapy parameter sets used by IMDs 14 may include a number of parameter sets programmed by one or more clinicians (not shown), and parameter sets representing adjustments made by patients 12 to these preprogrammed sets.

Each of systems 10 may also includes a clinician programmer 20 (illustrated as a part of system 10A in FIG. 1A). The clinician may use clinician programmer 20 to program therapy for patient 12A, e.g., specify a number of therapy parameter sets and provide the parameter sets to IMD 14A. The clinician may also use clinician programmer 20 to retrieve information collected by IMD 14A. The clinician may use clinician programmer 20 to communicate with IMD 14A both during initial programming of IMD 14A, and for collection of information and further programming during follow-up visits.

Clinician programmer 20 may, as shown in FIG. 1A, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

Systems 10 may also includes a patient programmer 26 (illustrated as part of system 10A in FIG. 1A), which also may, as shown in FIG. 1A, be a handheld computing device. Patient 12A may use patient programmer 26 to control the delivery of therapy by IMD 14A. For example, using patient programmer 26, patient 12A may select a current therapy parameter set from among the therapy parameter sets preprogrammed by the clinician, or may adjust one or more parameters of a preprogrammed therapy parameter set to arrive at the current therapy parameter set.

Patient programmer 26 may include a display 28 and a keypad 30, to allow patient 12A to interact with patient programmer 26. In some embodiments, display 28 may be a touch screen display, and patient 12A may interact with patient programmer 26 via display 28. Patient 12A may also interact with patient programmer 26 using peripheral pointing devices, such as a stylus, mouse, or the like.

Clinician and patient programmers 20, 26 are not limited to the hand-held computer embodiments illustrated in FIG. 1A. Programmers 20, 26 according to the invention may be any sort of computing device. For example, a programmer 20, 26 according to the invention may be a tablet-based computing device, a desktop computing device, or a workstation.

IMDs 14, clinician programmers 20 and patient programmers 26 may, as shown in FIG. 1A, communicate via wireless communication. Clinician programmer 20 and patient programmer 26 may, for example, communicate via wireless communication with IMD 14A using radio frequency (RF) telemetry or infrared techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, IMDs 14 collect patient posture information. Specifically, as will be described in greater detail below, IMDs 14 may monitor a plurality of signals, each of the signals generated by a respective sensor as a function of patient posture, and may identify posture events based on the signals. IMDs 14 may, for example, periodically identify the posture of patient 12 or transitions between postures made by patients 12 as posture events. For example, IMDs 14 may identify whether the patient is upright or recumbent, e.g., lying down, whether the patient is standing, sitting, or recumbent, or transitions between such postures. IMDs 14 may associate each determined posture event with the therapy parameter set that is currently active when the posture event is identified.

Over time, IMDs 14 use a plurality of therapy parameter sets to deliver the therapy to patients 12, and, as indicated above, may associate each identified posture event with a current set of therapy parameters. For each of a plurality of therapy parameter sets used by IMDs 14 over time, a processor within IMDs 14 or a computing device, such as clinician programmer 20 or patient programmer 26, may determine a value of one or more posture metrics based on the posture events associated with that therapy parameter set. A posture metric value may be, for example, an amount or percentage of time spent in a posture while a therapy parameter set is active, e.g., an average amount of time over a period of time, such as an hour, that patients 12 were within a particular posture. In some embodiments, a posture metric value may be an average number of posture transitions over a period of time, e.g., an hour.

In some embodiments, a plurality of posture metric values are determined for each of the plurality of therapy parameter sets. In such embodiments, an overall posture metric value may be determined. For example, the plurality of individual posture metric values may be used as indices to identify an overall posture metric value from a look-up table. The overall posture metric may selected from a predetermined scale of activity metric values, which may be numeric, such as activity metric values from 1-10.

One or more of IMDs 14 or a computing device may determine the posture metric values as described herein. In some embodiments, IMDs 14 determine and store posture metric values for each of a plurality of therapy parameter sets, and provide information identifying the therapy parameter sets and the associated posture metric values to a computing device, such as programmer 20. In other embodiments, IMDs 14 provide information identifying the therapy parameter sets and associated posture events to the computing device, and the computing devices determine the activity metric values for each of the therapy parameter sets using any of the techniques described herein with reference to IMDs 14. In still other embodiments, IMDs 14 provide signals output by sensors as function of patient posture to the computing device, or the computing devices receive the signals directed from the sensors via a wired or wireless link. In such embodiments, the computing device may identify posture events and determine posture metric values based on the signals using any of the techniques described herein with reference to IMDs 14.

In any of these embodiments, programmer 20 may present a list of the plurality of parameter sets and associated posture metric values to the clinician via display 22. Programmer 20 may order the list according to the posture metric values. Where values are determined for a plurality of posture metrics for each of the therapy parameter sets, programmer 20 may order the list according to the values of one of the posture metrics that is selected by the clinician. Programmer 20 may also present other posture information to the clinician, such as a trend diagram of posture over time, or a histogram or pie chart illustrating percentages of time that the patient assumed certain postures. Programmer 20 may generate such charts or diagrams using posture events associated with a particular one of the therapy parameter sets, or all of the posture events identified over a period of time.

However, the invention is not limited to embodiments that include programmer 20, or embodiments in which programmer presents posture information to the clinician. For example, in some embodiments, programmer 26 presents posture information as described herein to one or both of the clinician and patients 12. Further, in some embodiments, an external medical device comprises a display. In such embodiments, the external medical device may both determine posture metric values for the plurality of therapy parameter sets, and presents the list of therapy parameter sets and posture metric values. Additionally, in some embodiments, any type of computing device, e.g., personal computer, workstation, or server, may identify posture events, determine posture metric values, and/or present a list to a patient or clinician.

Figure 2A:
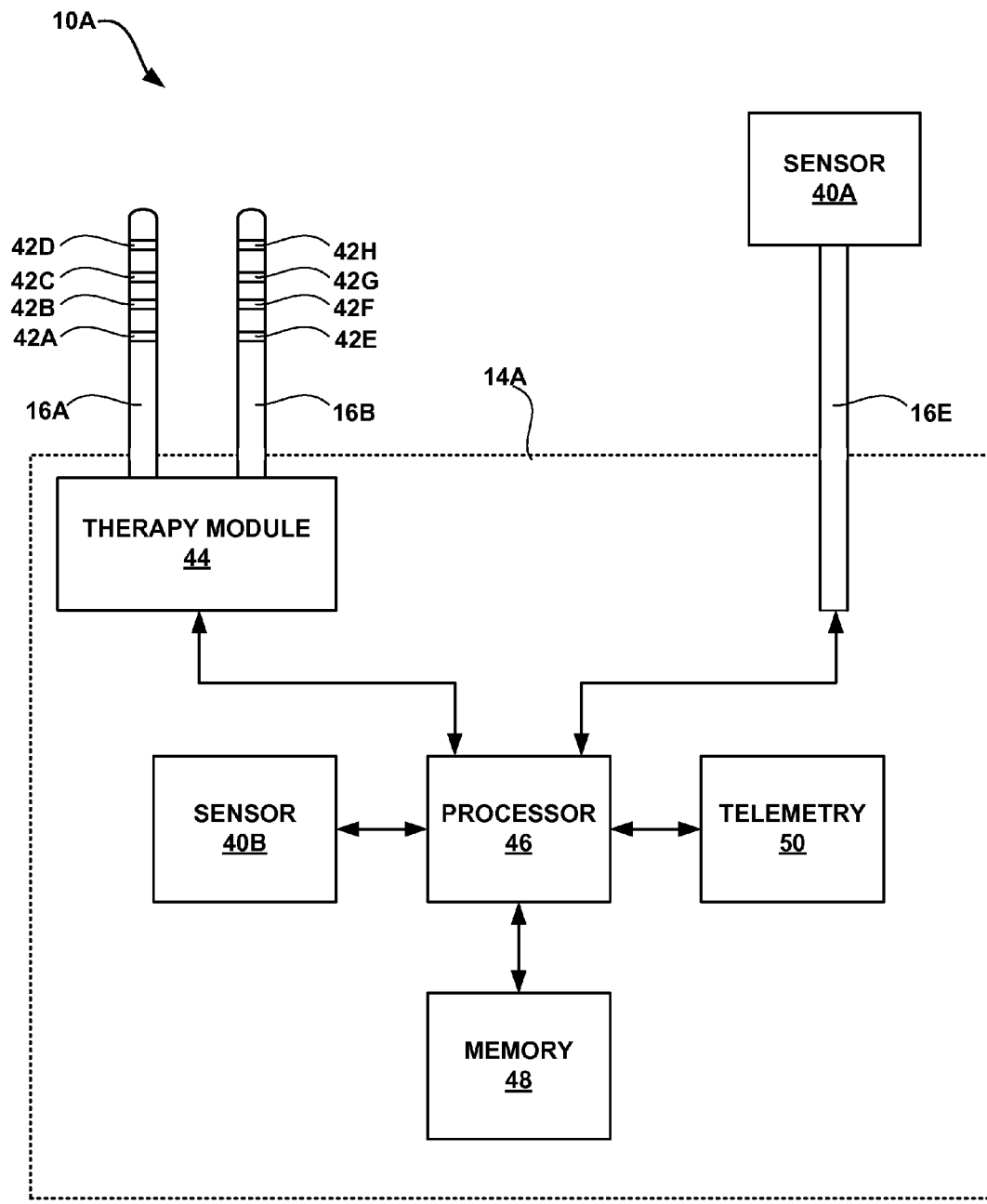
FIGS. 2A and 2B are block diagrams further illustrating the example systems and implantable medical devices of FIGS. 1A and 1B.
Figure 2B:
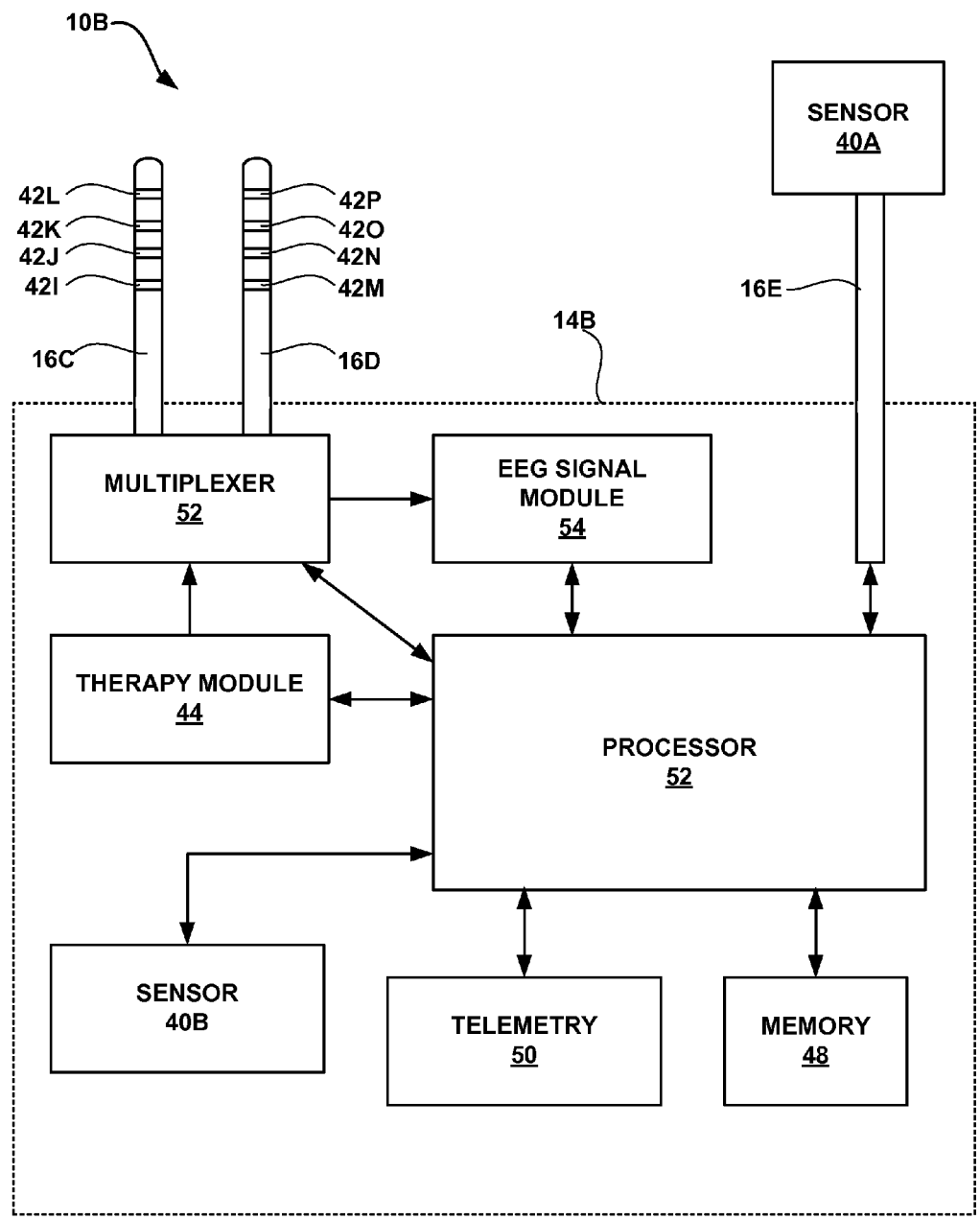

FIGS. 2A and 2B are block diagrams further illustrating systems 10A and 10B. In particular, FIG. 2A illustrates an example configuration of IMD 14A and leads 16A and 16B. FIG. 2B illustrates an example configuration of IMD 14B and leads 16C and 16D. FIGS. 2A and 2B also illustrate sensors 40A and 40B (collectively "sensors 40") that generate signals that vary as a function of patient posture. As will be described in greater detail below, IMDs 14 monitors the signals, and may identify posture events based on the signals.

IMD 14A may deliver neurostimulation therapy via electrodes 42A-D of lead 16A and electrodes 42E-H of lead 16B, while IMD 14B delivers neurostimulation via electrodes 42I-L of lead 16C and electrodes 42 M-P of lead 16D (collectively "electrodes 42"). Electrodes 42 may be ring electrodes. The configuration, type and number of electrodes 42 illustrated in FIGS. 2A and 2B are merely exemplary. For example, leads 16 may each include eight electrodes 42, and the electrodes 42 need not be arranged linearly on each of leads 16.

In each of systems 10A and 10B, electrodes 42 are electrically coupled to a therapy delivery module 44 via leads 16. Therapy delivery module 44 may, for example, include an output pulse generator coupled to a power source such as a battery. Therapy delivery module 44 may deliver electrical pulses to a patient 12 via at least some of electrodes 42 under the control of a processor 46, which controls therapy delivery module 44 to deliver neurostimulation therapy according to a current therapy parameter set. However, the invention is not limited to implantable neurostimulator embodiments or even to IMDs that deliver electrical stimulation. For example, in some embodiments a therapy delivery module 44 of an IMD may include a pump, circuitry to control the pump, and a reservoir to store a therapeutic agent for delivery via the pump.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 generates a signal that varies as a function of a patient 12 posture. IMDs 14 may include circuitry (not shown) that conditions the signals generated by sensors 40 such that they may be analyzed by processor 46. For example, IMDs 14 may include one or more analog to digital converters to convert analog signals generated by sensors 40 into digital signals usable by processor 46, as well as suitable filter and amplifier circuitry. Although shown as including two sensors 40, systems 10A and 10B may include any number of sensors.

Further, as illustrated in FIGS. 2A and 2B, sensors 40 may be included as part of IMDs 14, or coupled to IMDs 14 via leads 16. Sensors 40 may be coupled to IMDs 14 via therapy leads 16A-16D, or via other leads 16, such as lead 16E depicted in FIGS. 2A and 2B. In some embodiments, a sensor 40 located outside of an IMD 14 may be in wireless communication with processor 46. Wireless communication between sensors 40 and IMDs 14 may, as examples, include RF communication or communication via electrical signals conducted through the tissue and/or fluid of a patient 12.

Additionally, in some embodiments, sensors 40 may include one or more electrodes positioned within or proximate to the brain of patient 12, which detect electrical activity of the brain. For example, in embodiments in which an IMD 14 delivers stimulation or therapeutic agents to the brain, processor 46 may be coupled to electrodes implanted on or within the brain via a lead 16. System 10B, illustrated in FIGS. 1B and 2B, is an example of a system that includes electrodes 42, located on or within the brain of patient 12B, that are coupled to IMD 14B.

As shown in FIG. 2B, electrodes 42 may be selectively coupled to therapy module 44 or an EEG signal module 54 by a multiplexer 52, which operates under the control of processor 46. EEG signal module 54 receives signals from a selected set of the electrodes 42 via multiplexer 52 as controlled by processor 46. EEG signal module 54 may analyze the EEG signal for certain features indicative of sleep or different sleep states, and provide indications of relating to sleep or sleep states to processor 46. Thus, electrodes 42 and EEG signal module 54 may be considered another sensor 40 in system 10B. IMD 14B may include circuitry (not shown) that conditions the EEG signal such that it may be analyzed by processor 52. For example, IMD 14B may include one or more analog to digital converters to convert analog signals received from electrodes 42 into digital signals usable processor 46, as well as suitable filter and amplifier circuitry.

In some embodiments, processor 46 will only request EEG signal module 54 to operate when one or more other physiological parameters indicate that patient 12B is already asleep. However, processor 46 may also direct EEG signal module to analyze the EEG signal to determine whether patient 12B is sleeping, and such analysis may be considered alone or in combination with other physiological parameters to determine whether patient 12B is asleep. EEG signal module 60 may process the EEG signals to detect when patient 12 is asleep using any of a variety of techniques, such as techniques that identify whether a patient is asleep based on the amplitude and/or frequency of the EEG signals. In some embodiments, the functionality of EEG signal module 54 may be provided by processor 46, which, as described above, may include one or more microprocessors, ASICs, or the like.

Sensors 40 may include a plurality of accelerometers, gyros, or magnetometers that generate signals that indicate the posture of a patient 12. Sensors 40 may be oriented substantially orthogonally with respect to each other. In addition to being oriented orthogonally with respect to each other, each of sensors 40 used to detect the posture of patient 12 may be substantially aligned with an axis of the body of a patient 12. When accelerometers, for example, are aligned in this manner, the magnitude and polarity of DC components of the signals generate by the accelerometers indicate the orientation of the patient relative to the Earth's gravity, e.g., the posture of a patient 12. Further information regarding use of orthogonally aligned accelerometers to determine patient posture may be found in a commonly assigned U.S. Pat. No. 5,593,431, which issued to Todd J. Sheldon.

Other sensors 40 that may generate a signal that indicates the posture of a patient 12 include electrodes that generate a signal as a function of electrical activity within muscles of the patient 12, e.g., an electromyogram (EMG) signal, or a bonded piezoelectric crystal that generates a signal as a function of contraction of muscles. Electrodes or bonded piezoelectric crystals may be implanted in the legs, buttocks, chest, abdomen, or back of a patient 12, and coupled to IMDs 14 wirelessly or via one or more leads 16. Alternatively, electrodes may be integrated in a housing of the IMDs or piezoelectric crystals may be bonded to the housing when IMDs are implanted in the buttocks, chest, abdomen, or back of a patient 12. The signals generated by such sensors when implanted in these locations may vary based on the posture of a patient 12, e.g., may vary based on whether the patient is standing, sitting, or laying down.

Further, the posture of a patient 12 may affect the thoracic impedance of the patient. Consequently, sensors 40 may include an electrode pair, including one electrode integrated with the housing of IMDs 14 and one of electrodes 42, that generates a signal as a function of the thoracic impedance of a patient 12, and processor 46 may detect the posture or posture changes of the patient 12 based on the signal. The electrodes of the pair may be located on opposite sides of the patient's thorax. For example, the electrode pair may include one of electrodes 42 located proximate to the spine of a patient for delivery of SCS therapy, and IMD 14A with an electrode integrated in its housing may be implanted in the abdomen or chest of patient 12A.

Additionally, changes of the posture of a patient 12 may cause pressure changes with the cerebrospinal fluid (CSF) of the patient. Consequently, sensors 40 may include pressure sensors coupled to one or more intrathecal or intracerebroventricular catheters, or pressure sensors coupled to IMDs 14 wirelessly or via lead 16. CSF pressure changes associated with posture changes may be particularly evident within the brain of the patient, e.g., may be particularly apparent in an intracranial pressure (ICP) waveform.

Processor 46 may periodically determine the posture of a patient 12, and may store indications of the determined postures within memory 48 as posture events. Where systems 10 includes a plurality of orthogonally aligned sensors 40 located on or within the trunk of a patient 12, e.g., within IMDs 14 which is implanted within the abdomen of a patient 12 as illustrated in FIG. 1, processor 46 may be able to periodically determine whether patient is, for example, upright or recumbent, e.g., lying down. In embodiments of system 10 that include an additional one or more sensors 40 at other locations on or within the body of a patient 12, processor 46 may be able to identify additional postures of the patient 12. For example, in an embodiment of systems 10 that includes one or more sensors 40 located on or within the thigh of a patient 12, processor 46 may be able to identify whether the patient 12 is standing, sitting, or lying down. Processor 46 may also identify transitions between postures based on the signals output by sensors 40, and may store indications of the transitions, e.g., the time of transitions, as posture events within memory 48.

Processor 46 may identify postures and posture transitions by comparing the signals generated by sensors 40 to one or more respective threshold values. For example, when a patient 12 is upright a DC component of the signal generated by one of a plurality of orthogonally aligned accelerometers may be substantially at a first value, e.g., high or one, while the DC components of the signals generated by others of the plurality of orthogonally aligned accelerometers may be substantially at a second value, e.g., low or zero. When a patient 12 becomes recumbent, the DC component of the signal generated by one of the plurality of orthogonally aligned accelerometers that had been at the second value when the patient was upright may change to the first value, and the DC components of the signals generated by others of the plurality of orthogonally aligned accelerometers may remain at or change to the second value. Processor 46 may compare the signals generated by such sensors to respective threshold values to determine whether they are substantially at the first or second value, and to identify when the signals change from the first value to the second value.

Processor 46 may identify posture events continuously or periodically, e.g., one sample of the signals output by sensors 40 every minute or continuously for ten minutes each hour. In some embodiments, processor 46 limits recording of posture events to relevant time periods, i.e., when a patient 12 is awake or likely to be awake, and therefore likely to be active. For example, a patient 12 may indicate via patient programmer 26 when patient is going to sleep or awake. Processor 46 may receive these indications via a telemetry circuit 50 of IMDs 14, and may suspend or resume recording of posture events based on the indications. In other embodiments, processor 46 may maintain a real-time clock, and may record posture events based on the time of day indicated by the clock, e.g., processor 46 may limit posture event recording to daytime hours.

In some embodiments, processor 46 may determine when a patient 12 is attempting to sleep by receiving an indication from patient programmer 26. In other embodiments, processor 46 may monitor one or more physiological parameters of a patient 12 via signals generated by sensors 40, and may determine when the patient 12 is attempting to sleep or asleep based on the physiological parameters. For example, processor 46 may determine when the patient 12 is attempting to sleep by monitoring a physiological parameter indicative of patient physical activity. In some embodiments, processor 46 may determine whether a patient 12 is attempting to sleep by determining whether the patient 12 remains in a recumbent posture for a threshold amount of time.

In other embodiments, processor 46 determines when a patient 12 is attempting to fall asleep based on the level of melatonin in a bodily fluid. In such embodiments, a sensor 40 may take the form of a chemical sensor that is sensitive to the level of melatonin or a metabolite of melatonin in the bodily fluid, and estimate the time that the patient 12 will attempt to fall asleep based on the detection. For example, processor 46 may compare the melatonin level or rate of change in the melatonin level to a threshold level stored in memory 48, and identify the time that threshold value is exceeded. Processor 46 may identify the time that the patient 12 is attempting to fall asleep as the time that the threshold is exceeded, or some amount of time after the threshold is exceeded. Any of a variety of combinations or variations of the above-described techniques may be used to determine when a patient 12 is attempting to fall asleep, and a specific one or more techniques may be selected based on the sleeping and activity habits of a particular patient.

In order to determine whether a patient 12 is asleep, processor 46 may monitor any one or more physiological parameters that discernibly change when the patient 12 falls asleep, such as activity level, posture, heart rate, electrocardiogram (ECG) morphology, electroencephalogram (EEG) morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response. Processor 46 may additionally or alternatively monitor the variability of one or more of these physiological parameters, such as heart rate and respiration rate, which may discernible change when a patient 12 is asleep. Further details regarding monitoring physiological parameters to identify when a patient is attempting to sleep and when the patient is asleep may be found in a commonly-assigned and co-pending U.S. patent application Ser. No. 11/691,405 by Kenneth Heruth and Keith Miesel, entitled "DETECTING SLEEP," which was filed Mar. 26, 2007, issued as U.S. Pat. No. 8,055,348, and is incorporated herein by reference in its entirety.

In other embodiments, processor 46 may record posture events in response to receiving an indication from patient 12 via patient programmer 26. For example, processor 46 may record posture during times when a patient 12 believes the therapy delivered by IMD 14 is ineffective and/or the symptoms experienced by the patient 12 have worsened. In this manner, processor 46 may limit data collection to periods in which more probative data is likely to be collected, and thereby conserve a battery and/or storage space within memory 48.

Figure 3:
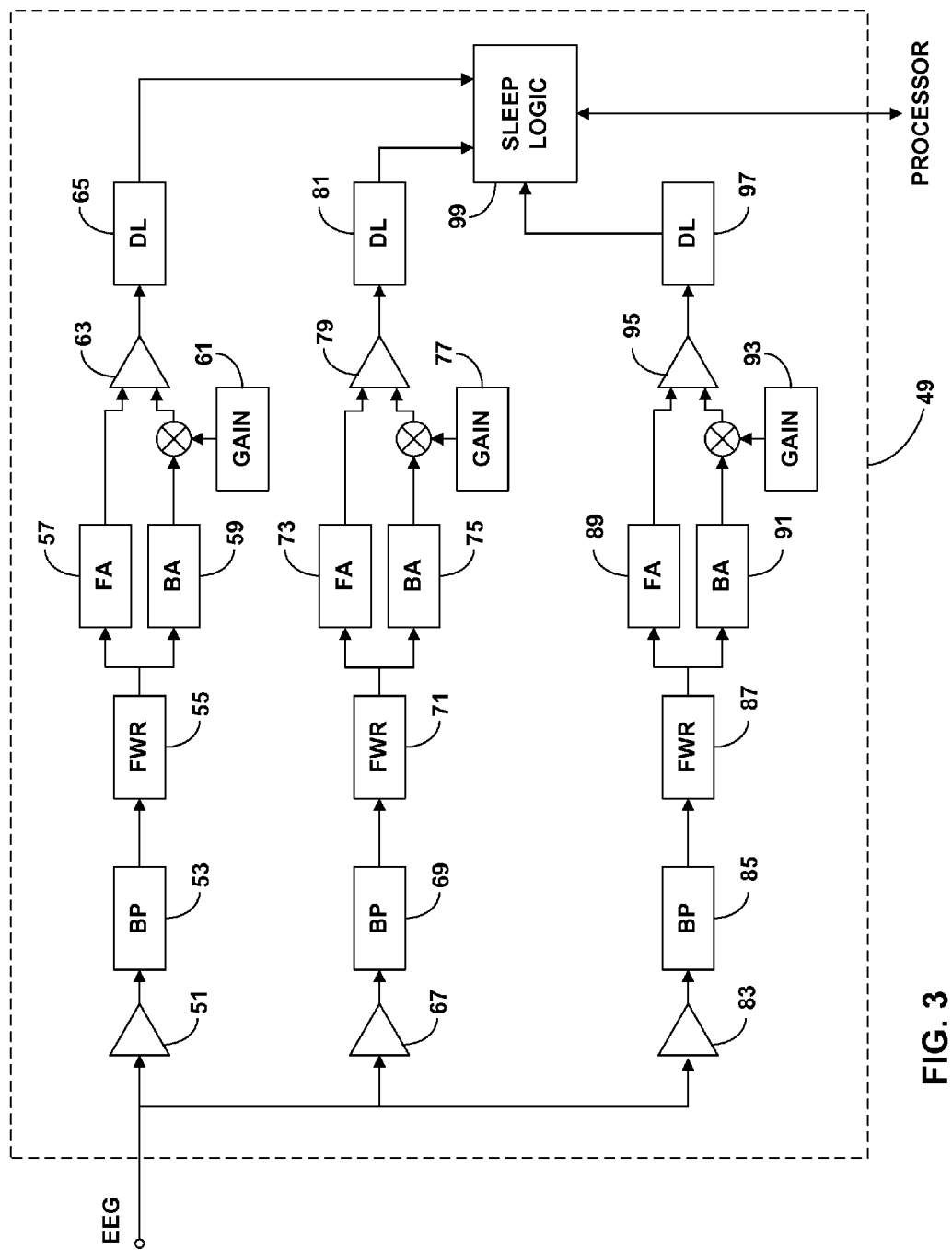
FIG. 3 is a logic diagram illustrating an example circuit that detects the sleep state of a patient from the electroencephalogram (EEG) signal.

FIG. 3 is a logical diagram of an example circuit that detects sleep and/or the sleep type of a patient based on the electroencephalogram (EEG) signal. Alternatively, the circuit may identify an awake state if a sleep state is not detected. As shown in FIG. 3, module 49 may be integrated into an EEG signal module of IMDs 14 or a separate implantable or external device capable of detecting an EEG signal. An EEG signal detected by electrodes adjacent to the brain of a patent 12 is transmitted into module 49 and provided to three channels, each of which includes a respective one of amplifiers 51, 67 and 83, and bandpass filters 53, 69 and 85. In other embodiments, a common amplifier amplifies the EEG signal prior to filters 53, 69 and 85.

Bandpass filter 53 allows frequencies between approximately 4 Hz and approximately 8 Hz, and signals within the frequency range may be prevalent in the EEG during S1 and S2 sleep states. Bandpass filter 69 allows frequencies between approximately 1 Hz and approximately 3 Hz, which may be prevalent in the EEG during the S3 and S4 sleep states. Bandpass filter 85 allows frequencies between approximately 10 Hz and approximately 50 Hz, which may be prevalent in the EEG during REM sleep. Each resulting signal may then processed to identify in which sleep state a patient 12 is.

After bandpass filtering of the original EEG signal, the filtered signals are similarly processed in parallel before being delivered to sleep logic module 99. For ease of discussion, only one of the three channels will be discussed herein, but each of the filtered signals would be processed similarly.

Once the EEG signal is filtered by bandpass filter 53, the signal is rectified by full-wave rectifier 55. Modules 57 and 59 respectively determine the foreground average and background average so that the current energy level can be compared to a background level at comparator 63. The signal from background average is increased by gain 61 before being sent to comparator 63, because comparator 63 operates in the range of millivolts or volts while the EEG signal amplitude is originally on the order of microvolts. The signal from comparator 63 is indicative of sleep stages S1 and S2. If duration logic 65 determines that the signal is greater than a predetermined level for a predetermined amount of time, the signal is sent to sleep logic module 99 indicating that patient 12 may be within the S1 or S2 sleep states. In some embodiments, as least duration logic 65, 81, 97 and sleep logic 99 may be embodied in a processor of the device containing EEG module 49.

Module 49 may detect all sleep types for a patient 12. Further, the beginning of sleep may be detected by module 49 based on the sleep state of a patient 12. Some of the components of module 49 may vary from the example of FIG. 3. For example, gains 61, 77 and 93 may be provided from the same power source. Module 49 may be embodied as analog circuitry, digital circuitry, or a combination thereof.

In other embodiments, FIG. 3 may not need to reference the background average to determine the current state of sleep of a patient 12. Instead, the power of the signals from bandpass filters 53, 69 and 85 are compared to each other, and sleep logic module 99 determines which the sleep state of patient 12 based upon the frequency band that has the highest power. In this case, the signals from full-wave rectifiers 55, 71 and 87 are sent directly to a device that calculates the signal power, such as a spectral power distribution module (SPD), and then to sleep logic module 99 which determines the frequency band of the greatest power, e.g., the sleep state of a patient 12. In some cases, the signal from full-wave rectifiers 55, 71 and 87 may be normalized by a gain component to correctly weight each frequency band.

Figure 4:
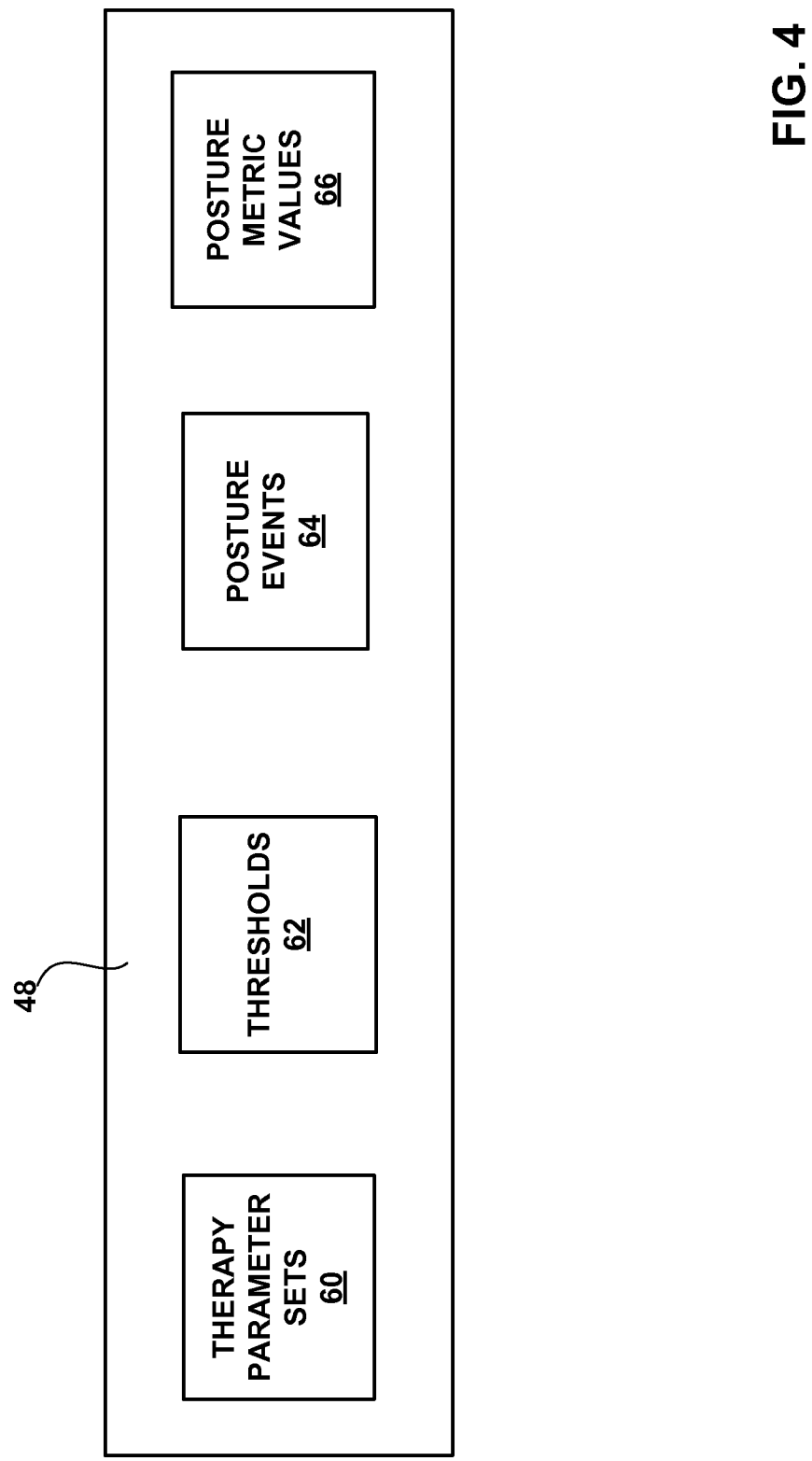
FIG. 4 is a block diagram illustrating an example memory of the implantable medical device of FIG. 1.

FIG. 4 illustrates memory 48 of IMDs 14 in greater detail. As shown in FIG. 4, memory 48 stores information describing a plurality of therapy parameter sets 60. Therapy parameter sets 60 may include parameter sets specified by a clinician using clinician programmer 20. Therapy parameter sets 60 may also include parameter sets that are the result of patient 12 changing one or more parameters of one of the preprogrammed therapy parameter sets. For example, a patient 12 may change parameters such as pulse amplitude, pulse frequency, or pulse width via patient programmer 26.

Memory 48 also stores thresholds 62 used by processor 46 to identify postures of patient 12 and/or transitions between postures, as discussed above. When processor 46 identifies a posture event 64 as discussed above, processor 46 associates the posture event 64 with the current one of therapy parameter sets 60, e.g., the one of therapy parameter sets 60 that processor 46 is currently using to control delivery of therapy by therapy module 44 to a patient 12. For example, processor 46 may store determined posture event 64 within memory 48 with an indication of the parameter sets 60 with which they are associated. In other embodiments, processor 46 stores samples (not shown) of signals generated by sensors 40 within memory 48 with an indication of the parameter sets 60 with which they are associated.

In some embodiments, processor 46 determines a value of one or more posture metrics for each of therapy parameter sets 60 based on the posture events 63 associated with the parameter sets 60. Processor 46 may store the determined posture metric values 66 within memory 48 with an indication as to which of therapy parameter sets 60 the determined values are associated with. For example, processor 46 may determine an amount of time that a patient 12 was in a posture when a therapy parameter set 60 was active, e.g., an average amount of time over a period of time such as an hour, as a posture metric 66 for the therapy parameter set 60. Processor 46 may additionally or alternatively determine percentages of time that patient 12 assumed one or more postures while a therapy parameter set was active as a posture metric 66 for the therapy parameter set 60. As another example, processor 46 may determine an average number of transitions over a period of time, such as an hour, when a therapy parameter set 60 was active as a posture metric 66 for the therapy parameter set 60.

In some embodiments, processor 46 determines a plurality of posture metric values 66 for each of the plurality of therapy parameter sets 60, and determines an overall posture metric value 66 for a parameter set based on the values of the individual posture metrics for that parameter set. For example, processor 46 may use the plurality of individual posture metric values as indices to identify an overall posture metric value from a look-up table stored in memory 48. Processor 46 may select the overall posture metric value from a predetermined scale of posture metric values, which may be numeric, such as posture metric values from 1-10.

As shown in FIGS. 2A and 2B, IMDs 14 includes a telemetry circuit 50, and processor 46 communicates with programmers 20, 26 via telemetry circuit 50. In some embodiments, processor 46 provides information identifying therapy parameter sets 60 and posture metric values 66 associated with the parameter sets to a programmer 20, 26 and the programmer displays a list of therapy parameter sets 60 and associated posture metric values 66. In other embodiments, as will be described in greater detail below, processor 46 does not determine posture metric values 66. Instead, processor 46 provides information describing posture events 64 to programmer 20, 26 via telemetry circuit 50, and the programmer determines posture metric values 66 for display to the clinician. Further, in other embodiments, processor 46 provides samples of signals generated by sensors 40 to programmer 20, 26 via telemetry circuit 50, and the programmer may identify both posture events 64 and determine posture metric values 66 based on the samples. In still other embodiments, one of programmers 20, 26 receives one or more of the signals generated by sensors 40 directly, and the programmer may both identify posture events 64 and determine posture metric values 66 based on the signals. Some external medical device embodiments of the invention include a display, and a processor of such an external medical device may both determine posture metric values 66 and display a list of therapy parameter sets 60 and associated posture metric values 66 to a clinician.

Figure 5:
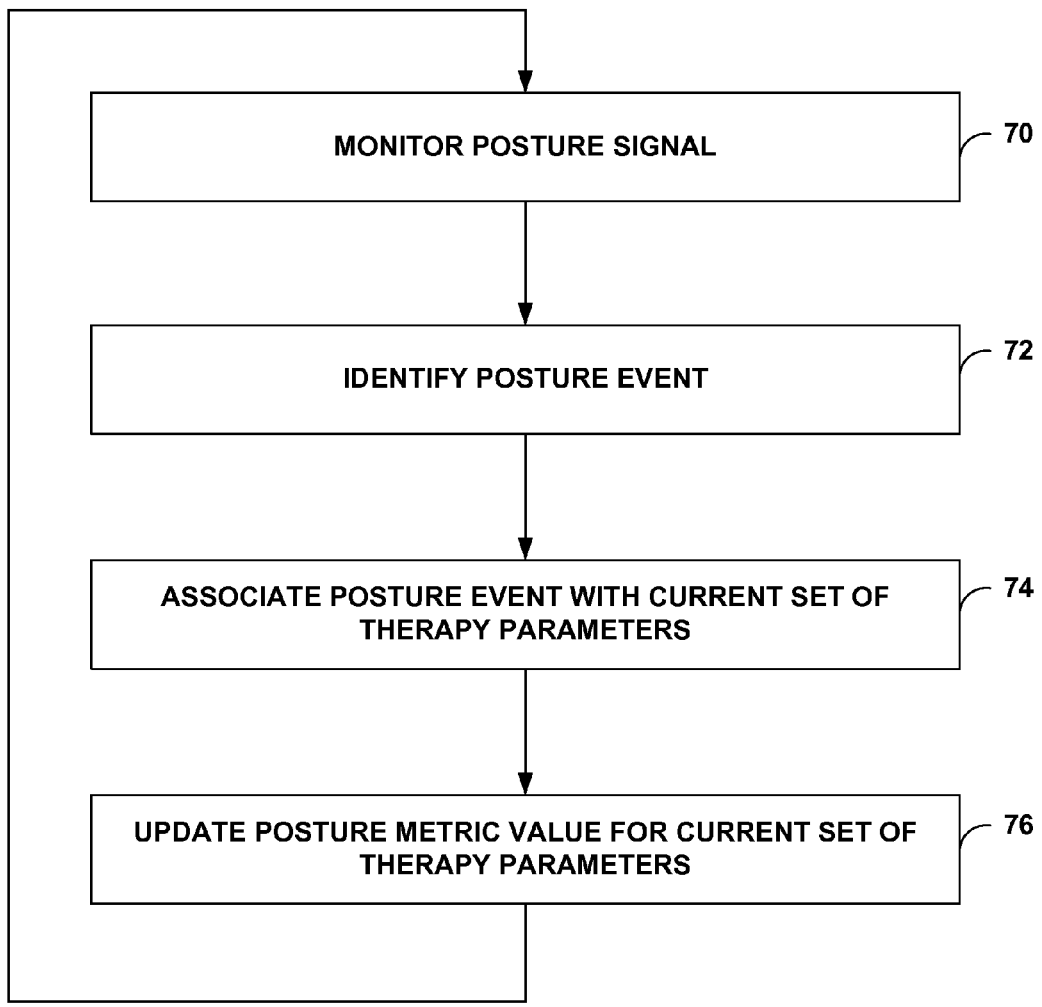
FIG. 5 is a flow diagram illustrating an example method for collecting activity information that may be employed by an implantable medical device.

FIG. 5 is a flow diagram illustrating an example method for collecting posture information that may be employed by IMDs 14. IMDs 14 monitor a plurality of signals generated by sensors 40 as a function of the posture of patient 12 (70). For example, IMDs 14 may monitor the DC components of signals generated by a plurality of substantially orthogonally aligned accelerometers. Each of the accelerometers may be substantially aligned with a respective axis of the body of a patient 12.

IMDs 14 identify a posture event 64 (72). For example, IMDs 14 may identify a current posture of a patient 12 at a time when the signals generated by sensors 40 are sampled, or may identify the occurrence of a transition between postures. IMDs 14 identify the current therapy parameter set 60, and associates the identified posture event 64 with the current therapy parameter set 60 (74). For example, IMDs 14 may store information describing the identified posture event 64 within memory 48 with an indication of the current therapy parameter set 60. IMDs 14 may then update one or more posture metric values 66 associated with the current therapy parameter set 60, as described above (76).

IMDs 14 may periodically perform the example method illustrated in FIG. 5, e.g., may periodically monitor the posture signals (70), identify posture events 64 (72), and associate the identified posture events 64 with a current therapy parameter set 60 (74). As described above, IMDs 14 may only perform the example method during daytime hours, or when patient is awake and not attempting to sleep, and/or only in response to an indication received from a patient 12 via patient programmer 26. IMDs 14 need not update posture metric values 66 each time a posture event 64 is identified, e.g., each time the posture signals are sampled to identify the posture of a patient 12. In some embodiments, for example, IMDs 14 may store posture events 64 within memory, and may determine the posture metric values 66 upon receiving a request for the values from clinician programmer 20.

Further, in some embodiments, as will be described in greater detail below, IMDs 14 do not determine the posture metric values 66, but instead provides information describing posture events 64 to a programming device, such as clinician programmer 20 or patient programmer 26. In such embodiments, the programming device determines the posture metric values 66 associated with each of the therapy parameter sets 60. Additionally, as described above, IMDs 14 need not identify posture events 64. Instead, a programming device may receive posture signals from IMDs 14 or directly from sensors 40, and may both identify posture events 64 and determine posture metric values 66 based on the samples.

Figure 6:
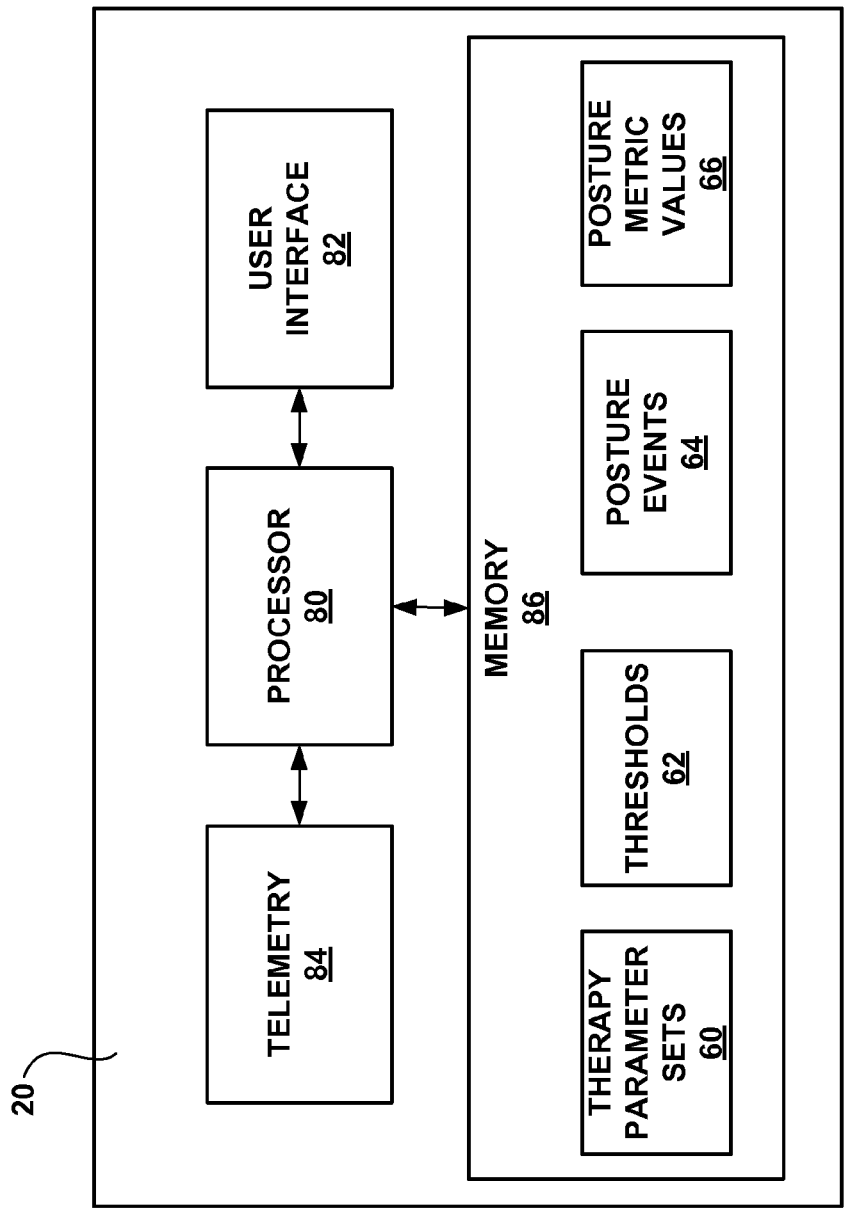
FIG. 6 is a block diagram illustrating an example clinician programmer.

FIG. 6 is a block diagram illustrating clinician programmer 20. A clinician may interact with a processor 80 via a user interface 82 in order to program therapy for a patient 12, e.g., specify therapy parameter sets. Processor 80 may provide the specified therapy parameter sets to IMDs 14 via telemetry circuit 84.

At another time, e.g., during a follow up visit, processor 80 may receive information identifying a plurality of therapy parameter sets 60 from IMDs 14 via telemetry circuit 84, which may be stored in a memory 86. The therapy parameter sets 60 may include the originally specified parameter sets, and parameter sets resulting from manipulation of one or more therapy parameters by a patient 12 using patient programmer 26. In some embodiments, processor 80 also receives posture metric values 66 associated with the therapy parameter sets 60, and stores the posture metric values 66 in memory 86.

In other embodiments, processor 80 receives information describing posture events 64 associated with the therapy parameter sets 60, and determines values 66 of one or more posture metrics for each of the plurality of therapy parameter sets 60 using any of the techniques described above with reference to IMDs 14 and FIGS. 2A, 2B, and 4. In still other embodiments, processor 80 receives the samples of the signals output by sensors 40 from IMDs 14, or directly from sensors 40, and identifies posture events 64 and determines posture metric values 66 based on signals using any of the techniques described above with reference to IMDs 14 and FIGS. 2A, 2B, and 4.

Upon receiving or determining posture metric values 66, processor 80 generates a list of the therapy parameter sets 60 and associated posture metric values 66, and presents the list to the clinician. User interface 82 may include display 22, and processor 80 may display the list via display 22. The list of therapy parameter sets 60 may be ordered according to the associated posture metric values 66. Where a plurality of posture metric values are associated with each of the parameter sets, the list may be ordered according to the values of the posture metric selected by the clinician. Processor 80 may also present other posture information to a user, such as a trend diagram of posture over time, or a histogram, pie chart, or other illustration of percentages of time that a patient 12 assumed certain postures. Processor 80 may generate such charts or diagrams using posture events 64 associated with a particular one of the therapy parameter sets 60, or all of the posture events recorded by IMDs 14.

User interface 82 may include display 22 and keypad 24, and may also include a touch screen or peripheral pointing devices as described above. Processor 80 may include a microprocessor, a controller, a DSP, an ASIC, an FPGA, discrete logic circuitry, or the like. Memory 86 may include program instructions that, when executed by processor 80, cause clinician programmer 20 to perform the functions ascribed to clinician programmer 20 herein. Memory 86 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

FIG. 7 illustrates an example list 90 of therapy parameter sets and associated posture metric values 66 that may be presented by clinician programmer 20. Each row of example list 130 includes an identification of one of therapy parameter sets 60, the parameters of the therapy parameter set, and values 66 associated with the therapy parameter set for each of two illustrated posture metrics. Programmer 20 may order list 90 according to a user-selected one of the posture metrics.

The posture metrics illustrated in FIG. 7 are a percentage of time upright, and an average number of posture transitions per hour. IMDs 14 or programmer 20 may determine the average number of posture transitions per hour for one of the illustrated therapy parameter sets by identifying the total number of posture transitions associated with the parameter set and the total amount of time that IMDs 14 was using the parameter set. IMDs 14 or programmer 20 may determine the percentage of time upright for one of parameter sets 60 as the percentage of the total time that the therapy parameter set was in use that a patient 12 was identified to be in an upright position.

Figure 8:
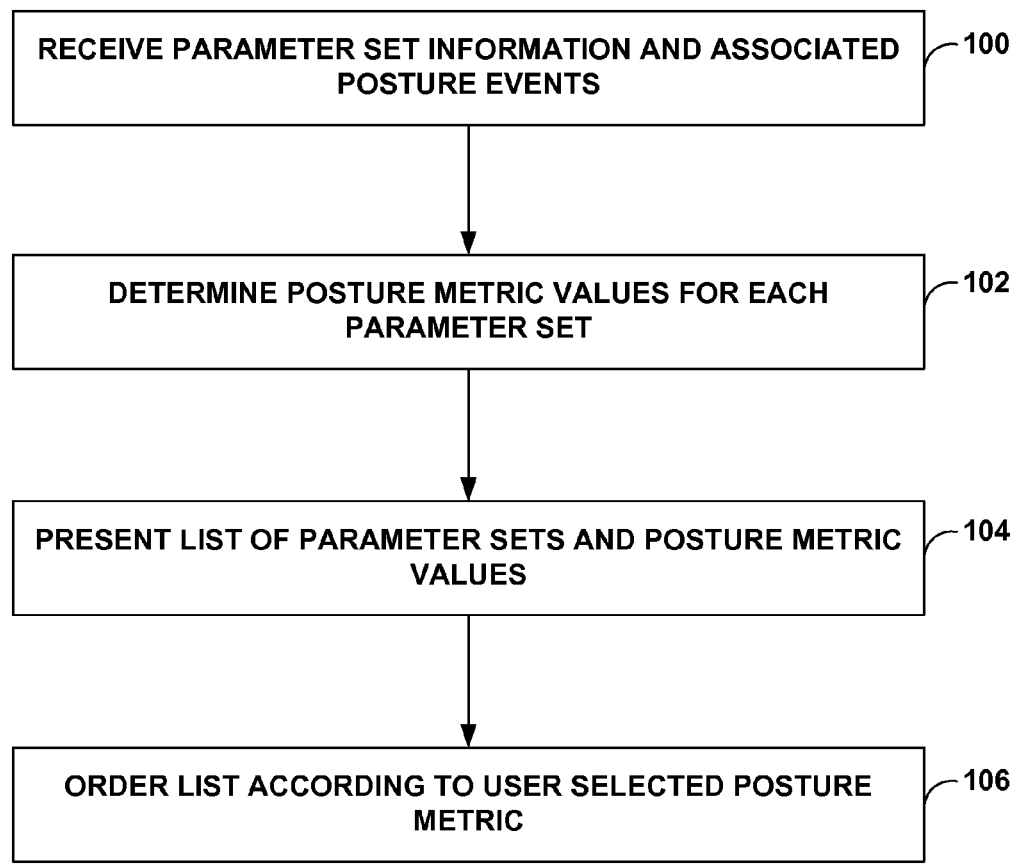
FIG. 8 is a flow diagram illustrating an example method for displaying a list of therapy parameter sets and associated activity metric values that may be employed by a clinician programmer.

FIG. 8 is a flow diagram illustrating an example method for displaying a list of therapy parameter sets 60 and associated posture metric values 66 that may be employed by a clinician programmer 20. Programmer 20 receives information identifying therapy parameter sets 60 and associated posture events from IMDs 14 (100). Programmer 20 then determines one or more posture metric values 66 for each of the therapy parameter sets based on the posture events 64 associated with the therapy parameter sets (102). In embodiments in which programmer 20 determines posture metric values 66, the clinician may be able to specify which of a plurality of possible posture metric values 66 are determined. In other embodiments, IMDs 14 determine the posture metric values 66, and provides them to programmer 20, or provides samples of posture signals associated with therapy parameter sets to programmer 20 for determination of posture metric values, as described above. After receiving or determining posture metric values 66, programmer 20 presents a list 90 of therapy parameter sets 60 and associated posture metric values 66 to the clinician, e.g., via display 22 (104). Programmer 20 may order list 90 of therapy parameter sets 60 according to the associated posture metric values 66, and the clinician may select the posture metric that list 90 is ordered according to via a user interface 82 (106).

The invention is not limited to embodiments in which the therapy delivering medical device monitors the posture or other physiological parameters of the patient described herein. In some embodiments, a separate monitoring device monitors the posture or other physiological parameters of the patient instead of, or in addition to, a therapy delivering medical device. The monitor may include a processor 46 and memory 48, and may be coupled to sensors 40, as illustrated above with reference to IMDs 14 and FIGS. 2A, 2B and 4. The monitor may identify posture events and posture metric values based on the signals received from the sensors, or may transmit posture events or the signals to a computing device for determination of posture metric values. In some embodiments, an external computing device, such as a programming device, may incorporate the monitor. The monitor may be external, and configured to be worn by a patient, such as on a belt around the waist or thigh of the patient.

Figure 9:
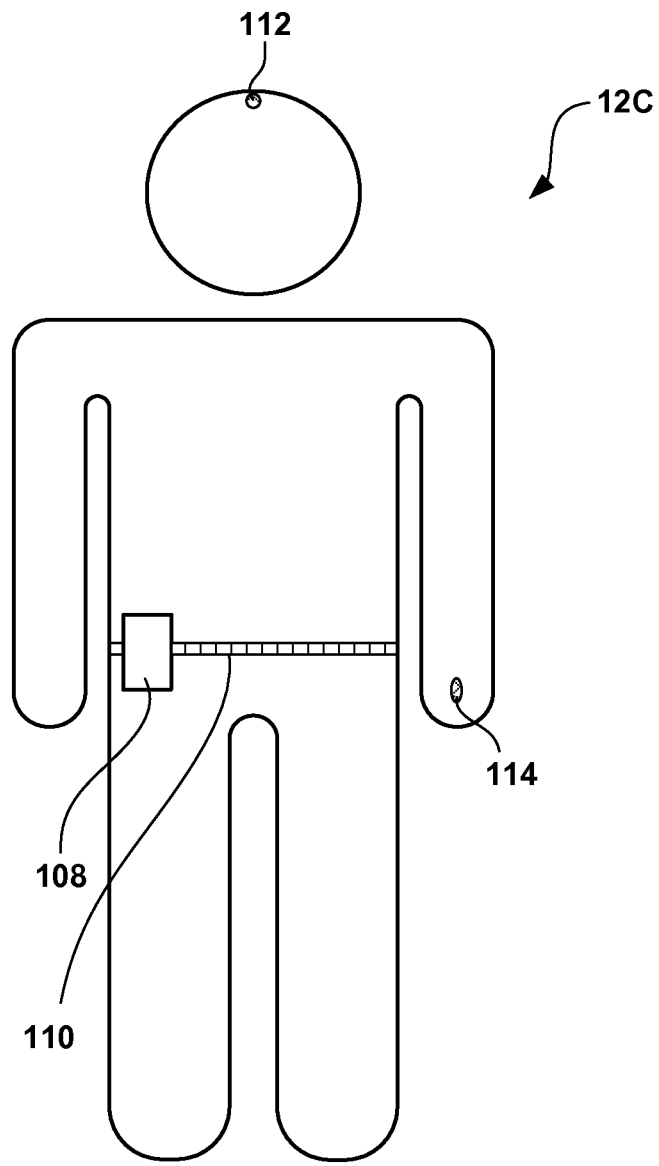
FIG. 9 is a conceptual diagram illustrating a monitor that monitors values of one or more accelerometers of the patient instead of, or in addition to, a therapy delivering medical device.

FIG. 9 is a conceptual diagram illustrating a monitor that monitors values of one or more accelerometers of the patient instead of, or in addition to, such monitoring being performed by a therapy delivering medical device. As shown in FIG. 9, patient 12C is wearing monitor 108 attached to belt 110.

Monitor 108 is capable of receiving measurements from one or more sensors located on or within patient 12C. In the example of FIG. 9, accelerometers 112 and 114 are attached to the head and hand of patient 12C, respectively. Accelerometers 112 and 114 may measure movement of the extremities, or activity level, of patient 12C to indicate when the patient moves instead of or in addition to identifying the posture of the patient. Alternatively, more or less accelerometers or other sensors may be used with monitor 108. The movement may be a posture event or other activity that is used to determine a posture metric.

Accelerometers 112 and 114 may be preferably multi-axis accelerometers, but single-axis accelerometers may be used. As patient 12C moves, accelerometers 112 and 114 detect this movement and send the signals to monitor 108. High frequency movements of patient 12C may be indicative of tremor, Parkinson's disease, or an epileptic seizure, and monitor 108 may be capable of indicating to IMDs 14, for example, that stimulation therapy must be changed to effectively treat the patient. In addition, accelerometers 112 and 114 may detect the posture of patient 12C in addition to or instead of other sensors 40. Accelerometers 112 and 114 may be worn externally, i.e., on a piece or clothing or a watch, or implanted at specific locations within patient 12C. In addition, accelerometers 112 and 114 may transmit signals to monitor 108 via wireless telemetry or a wired connection.

Monitor 108 may store the measurements from accelerometers 112 and 114 in a memory. In some examples, monitor 108 may transmit the measurements from accelerometers 112 and 114 directly to another device, such as IMDs 14, programming devices 20, 26, or other computing devices. In this case, the other device may analyze the measurements from accelerometers 112 and 114 to detect efficacy of therapy or control the delivery of therapy using any of the techniques described herein. In other embodiments, monitor 108 may analyze the measurements using the techniques described herein.

In some examples, a rolling window of time may be used when analyzing measurements from accelerometers 112 and 114. Absolute values determined by accelerometers 112 and 114 may drift with time or the magnitude and frequency of patient 12C movement may not be determined by a preset threshold. For this reason, it may be advantageous to normalize and analyze measurements from accelerometers 112 and 114 over a discrete window of time. For example, the rolling window may be useful in detecting epileptic seizures. If monitor 108 or IMDs 14 detects at least a predetermined number of movements over a 15 second window, an epileptic seizure may be most likely occurring. In this manner, a few quick movements from patient 12C not associated with a seizure may not trigger a response and change in therapy. The rolling window may also be used in detecting changes in posture with accelerometers 112 and 114 or other sensors as described herein.

Various embodiments of the invention have been described. However, one skilled in the art will recognize that various modifications may be made to the described embodiments without departing from the scope of the invention. For example, the invention may be implemented via any implantable or external, e.g., non-implantable, medical device, which may, but need not, deliver therapy.

As discussed above, the overall activity level of a patient, e.g., the extent to which the patient is on his or her feet or otherwise upright, moving, or otherwise active, rather than sitting, reclining, or lying in place, may be negatively impacted by any of a variety of ailments or symptoms. The frequency or amount of time that a patient is within upright postures, or the frequency of posture changes, may indicate how active the patient is. Accordingly, such posture metrics, as well as other posture metrics described above, may reflect the efficacy of a particular therapy or therapy parameter set in treating the ailment or symptom of the patient. In other words, it may generally be the case as the efficacy of a therapy parameter set increases, the extent to which the patient is active, e.g., the extent or frequency of upright postures or frequency of posture changes, may increase.

As discussed above, in accordance with the invention, posture events may be monitored during delivery of therapy according to a plurality of therapy parameter sets, and used to evaluate the efficacy of the therapy parameter sets. As an example chronic pain may cause a patient to avoid particular postures, or upright activity in general. Systems according to the invention may include any of a variety of medical devices that deliver any of a variety of therapies to treat chronic pain, such as SCS, DBS, cranial nerve stimulation, peripheral nerve stimulation, or one or more drugs. Systems may use the techniques of the invention described above to associate posture events and metrics with therapy parameter sets for delivery of such therapies, and thereby evaluate the extent to which a therapy parameter set is alleviating chronic pain by evaluating the extent to which the patient is upright and/or active during delivery of therapy according to the therapy parameter set.

As another example, psychological disorders, and particularly depression, may cause a patient to be inactive, despite a physical ability to be active. Often, a patient with depression will spend the significant majority of his or her day prone, e.g., in bed. Systems according to the invention may include any of a variety of medical devices that deliver any of a variety of therapies to treat a psychological disorder, such as DBS, cranial nerve stimulation, peripheral nerve stimulation, vagal nerve stimulation, or one or more drugs. Systems may use the techniques of the invention described above to associate posture events and metrics with therapy parameter sets for delivery of such therapies, and thereby evaluate the extent to which a therapy parameter set is alleviating the psychological disorder by evaluating the extent to which the therapy parameter set improves the overall activity level of the patient, e.g., causes the patient to be more frequently upright or to more frequently change postures.

Movement disorders, such as tremor, Parkinson's disease, multiple sclerosis, spasticity, or epilepsy may also affect the overall activity level of a patient, and the extent that the patient is in upright postures. In particular, the difficulties associated with performing activities and movement in general due to the movement disorder may cause a movement disorder patient to simply avoid such activity and spend a significant amount of time prone or seated. In addition, therapy may be directed to reducing or eliminating gait freeze common to Parkinson's disease patient. Systems according to the invention may include any of a variety of medical devices that deliver any of a variety of therapies to treat a movement disorders, such as DBS, cortical stimulation, or one or more drugs. Baclofen, which may or may not be intrathecally delivered, is an example of a drug that may be delivered to treat movement disorders. Both psychological disorders and movement disorders may be considered neurological disorders.

Systems may use the techniques of the invention described above to associate posture events and metrics with therapy parameter sets for delivery of such therapies. In this manner, such system may allow a user to evaluate the extent to which a therapy parameter set is alleviating the movement disorder by evaluating the extent to which the therapy parameter set improves the overall activity level of the patient, e.g., allows the patient feel able to be upright, moving, and engaging in tasks or activities.

Additionally, the invention is not limited to embodiments in which a programming device receives information from the medical device, or presents information to a user. Other computing devices, such as handheld computers, desktop computers, workstations, or servers may receive information from the medical device and present information to a user as described herein with reference to programmers 20, 26. A computing device, such as a server, may receive information from the medical device and present information to a user via a network, such as a local area network (LAN), wide area network (WAN), or the Internet. Further, in some embodiments, the medical device is an external medical device, and may itself include a display to present information to a user.

As another example, the invention may be embodied in a trial neurostimulator, which is coupled to percutaneous leads implanted within the patient to determine whether the patient is a candidate for neurostimulation, and to evaluate prospective neurostimulation therapy parameter sets. Similarly, the invention may be embodied in a trial drug pump, which is coupled to a percutaneous catheter implanted within the patient to determine whether the patient is a candidate for an implantable pump, and to evaluate prospective therapeutic agent delivery parameter sets. Posture metric values collected by the trial neurostimulator or pump may be used by a clinician to evaluate the prospective therapy parameter sets, and select parameter sets for use by the later implanted non-trial neurostimulator or pump. In particular, a trial neurostimulator or pump may determine values of one or more posture metrics for each of a plurality of prospective therapy parameter sets, and a clinician programmer may present a list of prospective parameter sets and associated posture metric values to a clinician. The clinician may use the list to identify potentially efficacious parameter sets, and may program a permanent implantable neurostimulator or pump for the patient with the identified parameter sets.

Further, the invention may be embodied as a computer-readable medium that includes instructions to cause a processor to perform any of the methods described herein. These and other embodiments are within the scope of the following claims.

The invention claimed is:

1. A medical system comprising:
a medical device that delivers a therapy to a patient according to therapy parameters that change over time according to a plurality of therapy parameter sets;
a sensor that generates a signal as a function of movement of the patient; and
a processor that:
monitors the signal generated by the sensor during the delivery of the therapy to the patient,
identifies a plurality of movement events based on the signal during the delivery of the therapy to the patient,
for each therapy parameter set in the plurality of therapy parameter sets, associates each of the movement events in the plurality of movement events that occur during the delivery of the therapy to the patient according that individual therapy parameter set with that individual therapy parameter set, and,
for each therapy parameter set in the plurality of therapy parameter sets, determines a value of a metric based on the movement events associated with that individual therapy parameter set, wherein the value of the metric indicates an efficacy of that individual therapy parameter set.

2. The medical system of claim 1, wherein at least one of the plurality of movement events comprises a movement indicative of at least one of tremor, Parkinson's disease, or an epileptic seizure.

3. The medical system of claim 1, wherein the signal comprises a signal generated by the sensor as a function of movement of one or more extremity of the patient.

4. The medical system of claim 1, wherein the medical device delivers at least one of a movement disorder therapy, psychological disorder therapy, or deep brain stimulation.

5. The medical system of claim 1, wherein the medical device delivers at least one of a tremor therapy, a Parkinson's disease therapy, and an epilepsy therapy.

6. The medical system of claim 1, further comprising a computing device that includes a display, wherein the computing device presents a list of the plurality of therapy parameter sets and metric values associated with the therapy parameter sets via the display.

7. The medical system of claim 6, wherein the computing device orders the list of therapy parameter sets according to the associated metric values.

8. The medical system of claim 7, wherein the processor determines a value of each of a plurality of metrics for each of a plurality of therapy parameter sets based on movement events associated with the therapy parameter sets, and the computing device orders the list according to a user selected one of the metrics.

9. The medical system of claim 1, further comprising a computing device that includes the display, wherein the computing device presents a graphical representation of the identified movement events via the display.

10. The medical system of claim 9, wherein the computing device presents at least one of a trend diagram, a histogram, or a pie chart based on the identified movement events.

11. A medical system comprising:
means for delivering a therapy to a patient according to therapy parameters that change over time according to a plurality of therapy parameter sets;
means for monitoring a signal generated by a sensor as a function of movement of a patient during the delivery of the therapy to the patient;
means for identifying a plurality of movement events based on the signal during the delivery of the therapy to the patient;
means for associating, for each therapy parameter set in the plurality of therapy parameter sets each of the movement events in the plurality of movement events that occur during the delivery of the therapy to the patient according that individual therapy parameter set with that individual therapy parameter set; and
means for determining, for each therapy parameter set in the plurality of therapy parameter sets, a value of a metric based on the movement events associated with that individual therapy parameter set, wherein the value of the metric indicates an efficacy of that individual therapy parameter set.

12. The medical system of claim 11, wherein the value of the metric represents an activity level of the patient.

13. The medical system of claim 1, wherein the value of the metric represents an activity level of the patient.

14. The medical system of claim 1, wherein the medical device is an implantable medical device.

15. The medical system of claim 1, wherein the medical device includes implantable lead including electrodes, wherein the medical device delivers the therapy to the patient via the electrodes.

16. The medical system of claim 1, wherein the medical device delivers deep brain stimulation.

17. The medical system of claim 1, wherein the medical device delivers spinal cord stimulation therapy.

18. The medical system of claim 1, wherein the medical device delivers pain therapy.

19. The medical system of claim 1, wherein the medical device delivers movement disorder therapy.

20. A medical system comprising:
- a medical device that delivers a therapy to a patient according to therapy parameters that change over time according to a plurality of therapy parameter sets;
- a sensor that generates a signal as a function of movement of the patient; and
- a processor that:
  - monitors the signal generated by the sensor during the delivery of the therapy to the patient,
  - identifies a plurality of movement events based on the signal during the delivery of the therapy to the patient,
  - for each therapy parameter set in the plurality of therapy parameter sets, associates each of the movement events in the plurality of movement events that occur during the delivery of the therapy to the patient according that individual therapy parameter set with that individual therapy parameter set, and,
  - for each therapy parameter set in the plurality of therapy parameter sets, determines a value of a metric based on the movement events associated with that individual therapy parameter set, wherein the value of the metric indicates an objective efficacy of that individual therapy parameter set.

* * * * *